(12) United States Patent
Aoki et al.

(10) Patent No.: US 6,916,638 B2
(45) Date of Patent: Jul. 12, 2005

(54) PROCESS FOR PRODUCING GLYCINE

(75) Inventors: Toshiya Aoki, Kurashiki (JP); Kiyoshi Kawakami, Yokohama (JP); Kazumasa Otsubo, Shizuoka-ken (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 147 days.

(21) Appl. No.: 10/168,096
(22) PCT Filed: Dec. 27, 2000
(86) PCT No.: PCT/JP00/09353
§ 371 (c)(1), (2), (4) Date: Jun. 17, 2002
(87) PCT Pub. No.: WO01/48234
PCT Pub. Date: Jul. 5, 2001

(65) Prior Publication Data
US 2003/0040085 A1 Feb. 27, 2003

(30) Foreign Application Priority Data
Dec. 27, 1999 (JP) .......................................... 11-370588

(51) Int. Cl.⁷ .............................................. C12P 13/04
(52) U.S. Cl. ..................................................... 435/106
(58) Field of Search ........................... 435/106; 455/106

(56) References Cited

U.S. PATENT DOCUMENTS

| | | |
|---|---|---|
| 3,940,316 A | 2/1976 | Commeryras et al. |
| 5,079,380 A | 1/1992 | Thunberg |
| 5,238,827 A * | 8/1993 | Shimizu et al. ............. 435/106 |
| 5,932,454 A | 8/1999 | Matsuoka et al. |

FOREIGN PATENT DOCUMENTS

| | | |
|---|---|---|
| EP | 0187680 B1 | 7/1986 |
| EP | 0332379 A2 | 9/1989 |
| EP | 0450885 A2 | 10/1991 |
| JP | 03280895 A | 12/1991 |
| WO | WO 80/01571 | 8/1980 |

OTHER PUBLICATIONS

Ingvorsen et al., Ciba Foundation Symposium, vol. 140, pp. 16–31, (1988).

* cited by examiner

Primary Examiner—Herbert J. Lilling
(74) Attorney, Agent, or Firm—Birch, Stewart, Kolasch & Birch, LLP

(57) ABSTRACT

Disclosed is a method for producing glycine, which comprises subjecting an aqueous solution of glycinonitrile to a hydrolysis reaction in a hydrolysis reaction system under the action of a microbial enzyme, thereby converting the glycinonitrile to glycine while by-producing ammonia, wherein the hydrolysis reaction system contains at least one organic impurity compound inhibiting the microbial enzyme, wherein the organic impurity compound has a molecular weight of 95 or more and contains at least one member selected from the group consisting of a nitrile group, a carboxyl group, an amide group, an amino group, a hydroxyl group and a trimethyleneamine structure, and wherein the hydrolysis reaction is performed under conditions wherein, during the hydrolysis reaction, the content of the organic impurity compound inhibiting the microbial enzyme in the hydrolysis reaction system is maintained at a level of 10% by weight or less, based on the weight of the hydrolysis reaction system.

32 Claims, 1 Drawing Sheet

PROCESS FOR PRODUCING GLYCINE

This application is the national phase under 35 U.S.C. § 371 PCT International Application No. PCT/JP00/09353 which has an International filing date of Dec. 27, 2000, which designated the United States of America.

BACKGROUND OF THE INVENTION

1. Field of the Invention

The present invention relates to a method for producing glycine. More particularly, the present invention is concerned with a method for producing glycine, which comprises subjecting an aqueous solution of glycinonitrile to a hydrolysis reaction in a hydrolysis reaction system under the action of a microbial enzyme, thereby converting the glycinonitrile to glycine while by-producing ammonia, wherein the hydrolysis reaction system contains at least one organic impurity compound inhibiting the microbial enzyme, wherein the organic impurity compound has a molecular weight of 95 or more and contains a specific structure, and wherein the hydrolysis reaction is performed under conditions wherein, during the hydrolysis reaction, the content of the organic impurity compound inhibiting the microbial enzyme in the hydrolysis reaction system is maintained at a level of 10% by weight or less, based on the weight of the hydrolysis reaction system. By the use of the method of the present invention, a high purity glycine which is useful as a food additive and as a raw material for synthesizing pharmaceuticals, agricultural chemicals and detergents can be produced easily and efficiently on a commercial scale without causing a heavy burden on the environment.

2. Prior Art

Conventionally, glycine has been produced by a process which comprises: synthesizing glycinonitrile from formaldehyde, hydrogen cyanide and ammonia by the Strecker method; converting the synthesized glycinonitrile into glycine soda and ammonia by hydrolysis using an alkali (such as caustic soda); neutralizing the glycine soda with an acid (such as sulfuric acid) to obtain glycine; and recovering the glycine by crystal-deposition (see Unexamined Japanese Patent Application Laid-Open Specification Nos. Sho 43-29929, Sho 51-19719, Sho 49-14420 and Sho 49-35329). As apparent from the above, such a conventional hydrolysis method employing a base uses an alkali and an acid in amounts each equivalent to the amount of glycine produced. Therefore, such method has a problem in that large amounts of salts are by-produced and the disposal of the by-products causes a heavy burden on the environment. Further, since the solubilities of the by-produced salts are similar to that of glycine, the recovery of glycine cannot be achieved by a single-step crystal-deposition and, therefore, a cumbersome operation, such as repetition of a cycle comprising crystal-deposition and circulation of a mother liquor, is necessary for recovering glycine (see Unexamined Japanese Patent Application Laid-Open Specification No. Sho 51-34113 (corresponding to DE 2541677-B and NL 7511023-B)). In addition, an aqueous glycinonitrile solution as an intermediate is unstable at a pH of 2.5 or more, and it is known that the higher the temperature, the greater the likelihood that glycinonitrile suffers denaturation, such as decomposition and discoloration (see Unexamined Japanese Patent Application Laid-Open Specification Nos. Sho 49-14420, Sho 54-46720 and Sho 54-46721). In "Kogyo Kagaku Zasshi (Journal of Industrial Chemistry)", Volume 70, page 54 (1967) published by Japanese Chemical Society, Japan, it is stated that hydrogen cyanide is likely to be denatured by polymerization under alkaline conditions, and black solids are generated as the polymerization proceeds. Further, "Jikken Kagaku Kouza (Lectures on Experimental Chemistry)", 1st ed., page 347, published by Japanese Chemical Society, Japan, describes that a cyanomethyl group of glycinonitrile and the like is likely to be denatured by addition polymerization under alkaline conditions, resulting in the generation of pyridine compounds and pyrimidine compounds. Unexamined Japanese Patent Application Laid-Open Specification No. Sho 62-212357 (corresponding to U.S. Pat. No. 4,661,614) discloses that an imine compound, such as iminodiacetonitrile, can be synthesized from formaldehyde, hydrogen cyanide and ammonia. Examined Japanese Patent Application Publication Specification No. Sho 51-244815 discloses that when glycinonitrile is heated, glycinonitrile generates ammonia and imine compounds (such as iminodiacetonitrile), and further heating causes the imine compounds to denature, resulting in the generation of black compounds. Therefore, in the conventional methods, a lowering of the yield of glycine due to the above-mentioned decomposition and denaturation is unavoidable. Further, the conventional methods have a defect in that a cumbersome treatment employing an activated carbon or a special ion exchange resin is necessary for removing a discolored matter (see Unexamined Japanese Patent Application Laid-Open Specification No. Hei 3-190851 and Unexamined Japanese Patent Application Laid-Open Specification No. Hei 4-226949 (corresponding to EP 459803-B)).

As a method for hydrolyzing glycinonitrile under moderate conditions without using large amounts of an alkali and an acid, there is known a method in which glycinonitrile is simply hydrolyzed using a microorganism having the activity to hydrolyze a nitrile group, thereby obtaining glycine and amxnonium. Examined Japanese Patent Application Publication Specification No. Sho 58-15120 (corresponding to French Patent No. 225585) discloses a method in which a hydrolysis reaction is conducted using *Brevibacterium* R312 suspended in a reaction medium liquid which has been adjusted to have a pH value of 8 with caustic potash or the like. Examined Japanese Patent Application No. Hei 3-62391 (corresponding to EP 187680-B) discloses a method in which a hydrolysis reaction is conducted using *Corynebacterium* N-774 suspended in a reaction medium liquid which is a phosphate buffer having a pH value of 7.7. Unexamined Japanese Patent Application Laid-Open Specification No. Hei 3-280889 (corresponding to EP 450885-B) discloses a method in which glycine is produced from glycinonitrile by using a microorganism belonging to the genus *Rhodococcus, Arthrobacter, Caseobacter, Pseudomonas, Enterobacter, Acinetobacter, Alkaligenes, Corynebacterium* or *Streptomyces* which is capable of hydrolyzing a nitrile group, wherein the microorganism is suspended in a reaction medium liquid which is a phosphate buffer having a pH value of 7.7. However, as shown in the working examples of these patent documents, these methods require that a lyophilized microorganism be used in an amount which is equal to or greater than the amount of glycine, or alternatively, the reaction be performed for 30 hours using a large amount of a lyophilized microorganism, namely 5% by weight or more, based on the weight of glycine. Further, as also shown in the working examples of these patent documents, these methods require that a neutralizing agent be successively added to the reaction system to maintain the pH of the reaction system within the neutral range so as to maintain the activity of the microorganism. In general, for neutralizing an ammonium salt of glycine, sulfuric acid or phosphoric acid is added to the reaction system, and hence a large amount of ammonium sulfate or ammonium phosphate is likely to remain in the reaction system. Therefore, the above-mentioned methods for producing glycine by using a microorganism are disadvantageous in that a large amount of an acid must be used and a large amount of waste must be discarded. Further, the abovementioned methods using a microorganism have the following problems. In the above-mentioned methods using a microorganism, the operation for recovering glycine needs a step of adding methanol or the like in addition to the concentration step, so that the operation for recovering glycine becomes complicated, as compared to the case of the alkaline hydrolysis method mentioned above (see Examined Japanese Patent Application Publication Specification No. Sho 58-15120 (corresponding to French Patent No. 225565)) . Further, the above-mentioned methods use a large amount of a microorganism, and this results in a further increase in the amount of waste. On the other hand, a method is known which employs a microorganism and electric dialysis and in which glycine and ammonia are separately recovered while recycling an alkali (see Unexamined Japanese Patent Application Laid-Open Specification No. Sho 10-179183 (corresponding to U.S. Pat. No. 5,932,454 and EP 852261-A)). This method is a method for producing glycine, comprising the following steps: a step of producing amrnonium salts of organic acids (including glytine) by using a microorganism; a step of converting the amrnonium salts into alkali salts, thereby eliminating ammonia; a step of recovering the eliminated ammonia; a step of separating the alkali and the organic acids from each other by electric dialysis; a step of extracting the organic acids with an organic solvent; and a step of separating the organic acids from the organic solvent. In the working examples of the above-mentioned patent document, only 0.3 mole of an organic acid is obtained from the microorganism cultured in 20 g of glycerin medium, showing that the activity of the microorganism is very low. Thus, this method has disadvantages in that multiple steps and cumbersome operations are necessary, a large amount of electricity is consumed, and a large amount of a microorganism is used and discarded.

As apparent from the above, the conventional methods for producing glycine from glycinonitrile by the use of a microorganism have disadvantages in that both the activity per unit amount of a lyophilized microorganism and the activity per unit time are low, and large amounts of culture medium and microorganism must be discarded. In addition, in the case of a method in which the electric dialysis is not employed, there are problems in that the recovery of ammonia is difficult due to the use of a neutralizing agent for adjusting the pH of the reaction system or for recovering glycine, and that a step of removing the neutralizing agent is necessary. Even in the case of a method in which the electric dialysis is employed, the recovery of ammonia requires not only electricity but also a cumbersome, multiple-step operation. Therefore, the commercial practice of this method cannot be satisfactorily performed.

SUMMARY OF THE INVENTION

In this situation, the present inventors have made extensive and intensive studies for finding a reaction method and reaction conditions which can solve the above-mentioned problems, and for finding microorganisms which are suitable for use in such a reaction method. As a result, it has unexpectedly been found that the above-mentioned objective can be attained by a method for producing glycine, which comprises: subjecting an aqueous solution of glycinonitrile to a hydrolysis reaction in a hydrolysis reaction system under the action of a microbial enzyme, thereby converting the glycinonitrile to glycine while by-producing ammonia, wherein the hydrolysis reaction system contains at least one organic impurity compound inhibiting the microbial enzyme, wherein the organic impurity compound has a molecular weight of 95 or more and contains a specific structure, and wherein the hydrolysis reaction is performed under conditions wherein, during the hydrolysis reaction, the content of the organic impurity compound inhibiting the microbial enzyme in the hydrolysis reaction system is maintained at a level of 10% by weight or less, based on the weight of the hydrolysis reaction system. That is, it has surprisingly been found that by the use of the above-mentioned method, advantages are achieved only in that glycine can be produced without the need to use and discard large amounts of a microorganism, a culture medium, an acid, an alkali and the like, but also in that the discoloration of glycine can be suppressed, and both the glycine production activity per unit weight of a microorganism and the glycine production activity per unit time become high, and both glycine and ammonia can be stoichiometrically produced without decomposition or consumption thereof and can be separately and easily recovered. The present invention has been completed, based on the above-mentioned novel findings.

Accordingly, it is a primary object of the present invention to provide a method for producing glycine, which is advantageous not only in that high purity glycine and high purity ammonia can be produced efficiently and stoichiometrically and can be separately recovered, but also in that the method does not cause a heavy burden on the environment.

The foregoing and other objects, features and advantages of the present invention will be apparent to those skilled in the art from the following detailed description and the appended claims taken in connection with the accompanying drawings.

Figure 1:
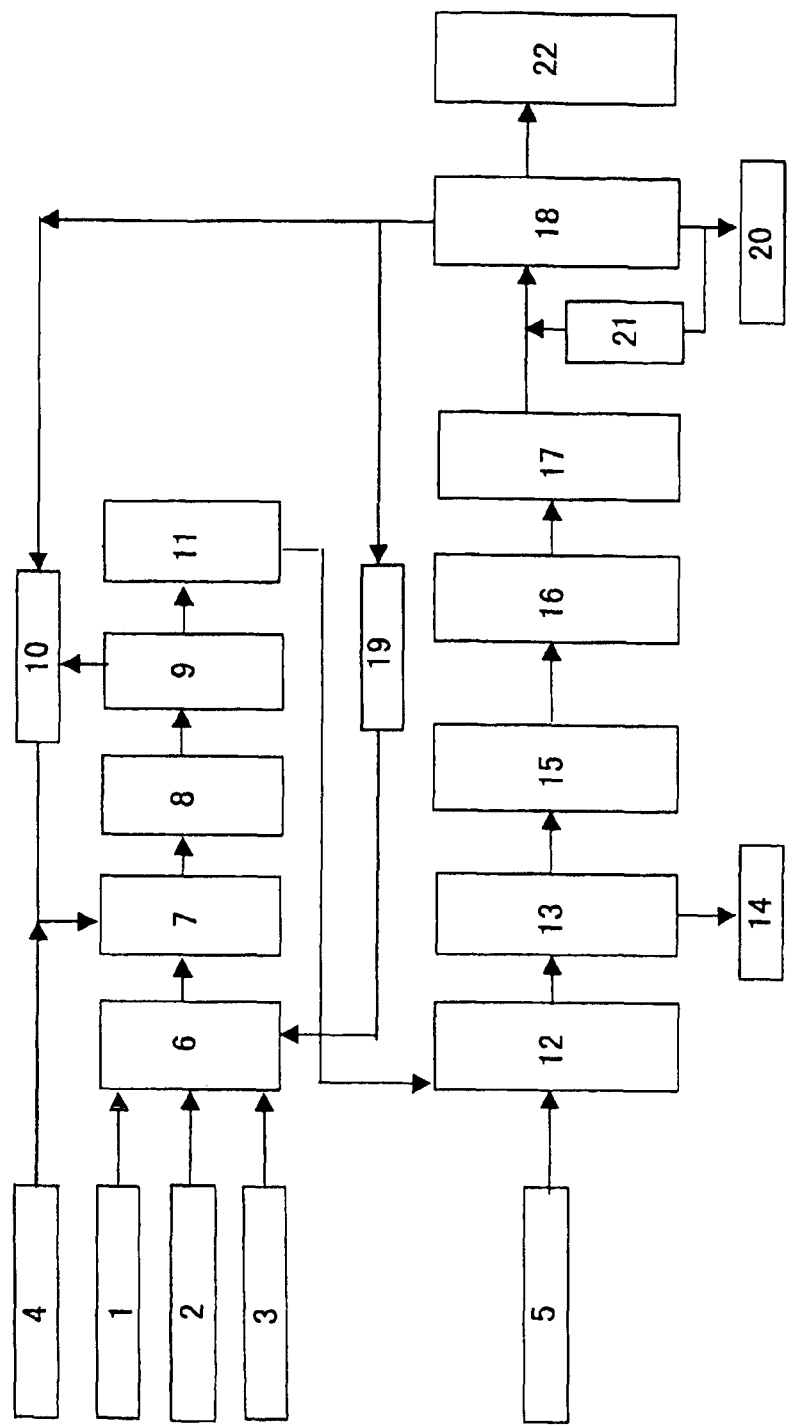
FIG. 1 is a diagram showing the production system used in Example 12 for producing glycine.

| Description of Reference Numerals | |
|---|---|
| 1: | aqueous formaldehyde solution |
| 2: | liquid hydrogen cyanide |
| 3: | sodium hydroxide |
| 4: | gaseous ammonia |
| 5: | microbial suspension |
| 6,7,8: | autoclave |
| 9: | flash distillation apparatus |
| 10: | liquid ammonia |
| 11,16: | intermediate tank |
| 12: | hydrolysis reactor |
| 13: | continuous centrifuge |
| 14: | microorganism to be discarded |
| 15: | circulation type ultrafiltration apparatus |
| 17: | activated carbon column |
| 18: | continuous crystal-deposition apparatus |
| 19: | water which has been evaporated and recovered |
| 20: | blow |
| 21: | filtrate |
| 22: | glycine crystals |

DETAILED DESCRIPTION OF THE INVENTION

In one aspect of the present invention, there is provided a method for producing glycine, comprising:

providing glycinonitrile in the form of an aqueous solution thereof, subjecting the aqueous solution of glycinonitrile to a hydrolysis reaction in a hydrolysis reaction system under the action of a microbial enzyme having the activity to hydrolyze a nitrile group, thereby converting the glycinonitrile to glycine while by-producing ammonia, the hydrolysis reaction system containing at least one organic impurity compound inhibiting the microbial enzyme, wherein the at least one organic impurity compound inhibiting the microbial enzyme has a molecular weight of 95 or more and contains at least one member selected from the group consisting of a nitrile group, a carboxyl group, an amide group, an amino group, a hydroxyl group and a trimethyleneamine structure, wherein the trimethyleneamine structure has a skeleton represented by the following formula (1):

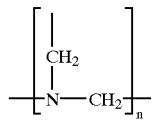

(1)

wherein n represents an integer of 1 or more, the hydrolysis reaction being performed under conditions wherein, during the hydrolysis reaction, the content of the organic impurity compound inhibiting the microbial enzyme in the hydrolysis reaction system is maintained at a level of 10% by weight or less, based on the weight of the hydrolysis reaction system, and isolating the glycine from the hydrolysis reaction system.

For easy understanding of the present invention, the essential features and various preferred embodiments of the present invention are enumerated below.

1. A method for producing glycine, comprising:
    providing glycinonitrile in the form of an aqueous solution thereof,
    subjecting the aqueous solution of glycinonitrile to a hydrolysis reaction in a hydrolysis reaction system under the action of a microbial enzyme having the activity to hydrolyze a nitrile group, thereby converting the glycinonitrile to glycine while by-producing ammonia,
    the hydrolysis reaction system containing at least one organic impurity compound inhibiting the microbial enzyme, wherein the at least one organic impurity compound inhibiting the microbial enzyme has a molecular weight of 95 or more and contains at least one member selected from the group consisting of a nitrile group, a carboxyl group, an amide group, an amino group, a hydroxyl group and a trimethyleneamine structure, wherein the trimethyleneamine structure has a skeleton represented by the following formula (1):

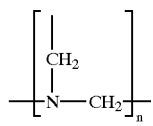

(1)

wherein n represents an integer of 1 or more,
the hydrolysis reaction being performed under conditions wherein, during the hydrolysis reaction, the content of the organic impurity compound inhibiting the microbial enzyme in the hydrolysis reaction system is maintained at a level of 10% by weight or less, based on the weight of the hydrolysis reaction system, and isolating the glycine from the hydrolysis reaction system.

2. The method according to item 1 above, wherein the at least one organic impurity compound inhibiting the microbial enzyme is produced as a by-product in at least one reaction selected from the group consisting of the synthesis of glycinonitrile from hydrogen cyanide, formaldehyde and ammonia, and the hydrolysis of the glycinonitrile into glycine and ammonia.

3. The method according to item 1 or 2 above, wherein the at least one organic impurity compound inhibiting the microbial enzyme comprises a compound represented by the following formula (2):

$$NH_{3-n}(CH_2Y^1)_n \qquad (2)$$

wherein each $Y^1$ independently represents a nitrile group, a carboxyl group or an amide group; and n represents an integer of 2 or 3.

4. The method according to item 1 or 2, wherein the at least one organic impurity compound inhibiting the microbial enzyme comprises at least one compound selected from the group consisting of the following compounds (a) and (b):

(a) a compound represented by the following formula (3):

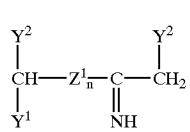

(3)

wherein:

$Y^1$ represents a nitrile group, a carboxyl group or an amide group;

each $Y^2$ independently represents an amino group or a hydroxyl group;

n represents an integer of 0 or more; and the or each $Z^1$ is independently represented by the following formula (4) or (5):

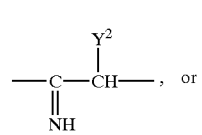

(4)

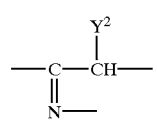

(5)

wherein each $Y^2$ independently represents an amino group or a hydroxyl group, and (b) a compound represented by the following formula (6) or (7):

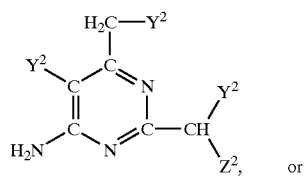
(6)

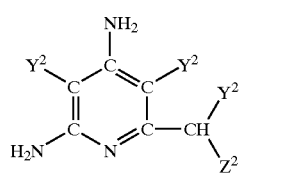
(7)

wherein each $Y^2$ independently represents an amino group or a hydroxyl group; and each $Z^2$ is independently represented by the following formula (8) or (9):

(8)

or $Z^1{}_n\text{-H}$ (9)

wherein:
$Y^2$ represents an amino group or a hydroxyl group; the or each $Z^1$ is as defined for formula (3); and n represents an integer of 0 or more.

5. The method according to item 1 or 2 above, wherein the at least one organic impurity compound inhibiting the microbial enzyme comprises at least one compound selected from the group consisting of the following compounds (c) and (d):

(c) a compound represented by the following formula (10) or (11):

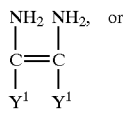
(10)

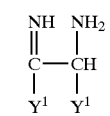
(11)

wherein each $Y^1$ independently represents a nitrile group, a carboxyl group or an amide group, and (d) a compound represented by the following formula (12):

$(HCN)_n$ (12)

wherein n represents an integer of 4 or more.

6. The method according to item 1 or 2 above, wherein the at least one organic impurity compound inhibiting the microbial enzyme comprises a compound having in a molecule thereof at least one skeleton selected from the group consisting of the following skeletons (e) and (f):

(e) a skeleton represented by the following formula (13):

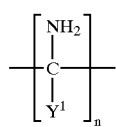
(13)

wherein each $Y^1$ independently represents a nitrile group, a carboxyl group or an amide group; and n represents an integer of 2 or more, and (f) a skeleton represented by the following formula (14) or (15):

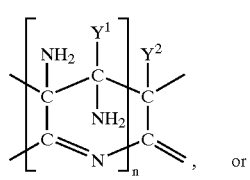
(14)

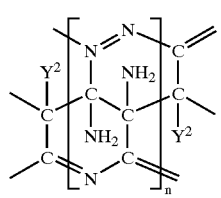
(15)

wherein:
the or each $Y^1$ independently represents a nitrile group, a carboxyl group or an amide group;
each $Y^2$ independently represents an amino group or a hydroxyl group; and
n represents an integer of 1 or more.

7. The method according to item 1 or 2 above, wherein the at least one organic impurity compound inhibiting the microbial enzyme comprises a compound having in a molecule thereof at least one skeleton selected from the group consisting of the following skeletons (g) and (h):

(g) a skeleton represented by the following formula (16):

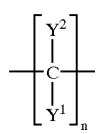
(16)

wherein:
each $Y^1$ independently represents a nitrile group, a carboxyl group or an amide group;
each $Y^2$ independently represents an amino group or a hydroxyl group;
and n represents an integer of 2 or more, and (h) a skeleton represented by the following formula (17) or (18):

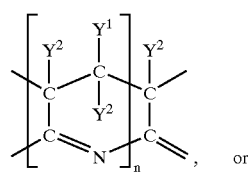
(17)

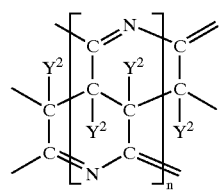
(18)

wherein:
the or each $Y^1$ independently represents a nitrile group, a carboxyl group or an amide group;
each $Y^2$ independently represents an amino group or a hydroxyl group; and
n represents an integer of 1 or more.

8. The method according to item 1 or 2 above, wherein the at least one organic impurity compound inhibiting the microbial enzyme comprises hexamethylenetetramine.

9. The method according to any one of items 1 to 8 above, wherein the at least one organic impurity compound inhibiting the microbial enzyme exhibits a peak between 53 ppm and 100 ppm in a $^{13}$C-NMR spectrum as measured in heavy water.

10. The method according to any one of items 1 to 9 above, wherein the at least one organic impurity compound inhibiting the microbial enzyme exhibits absorption maximums between 340 nm and 380 nm and between 440 nm and 480 nm in an ultraviolet-visible absorption spectrum as measured with respect to the hydrolysis reaction system.

11. The method according to any one of items 1 to 10 above, wherein the at least one organic impurity compound inhibiting the microbial enzyme has a molecular weight of 130 or more.

12. The method according to any one of items 1 to 11 above, wherein the amount of the at least one organic impurity compound inhibiting the microbial enzyme is 1% by weight or less, based on the weight of the hydrolysis reaction system.

13. The method according to any one of items 1 to 12 above, wherein the hydrolysis reaction system has oxygen dissolved therein in an amount of 5 ppm by weight or less, based on the weight of the hydrolysis reaction system.

14. The method according to any one of items 1 to 13 above, wherein the hydrolysis is conducted using a closed reaction system, a reaction system which is pressurized with an inert gas, a reaction system through which an inert gas is flowed or a reaction system which is under a pressure of less than atmospheric pressure, so that the amount of oxygen dissolved in the hydrolysis reaction system is suppressed.

15. The method according to any one of items 1 to 14 above, wherein the hydrolysis is conducted in the hydrolysis reaction system having ammonia dissolved therein.

16. The method according to any one of items 1 to 15 above, wherein the hydrolysis is conducted in the hydrolysis reaction system containing an electrolyte in an amount of 2% by weight or less, based on the weight of the glycinonitrile.

17. The method according to any one of items 1 to 16 above, wherein the microbial enzyme having the activity to hydrolyze a nitrile group is derived from a microorganism belonging to a genus selected from the group consisting of *Acinetobacter, Rhodococcus, Corynebacterium, Alcaligenes, Mycobacterium, Rhodopseudomonas* and *Candida*.

18. The method according to item 17 above, wherein the microbial strain of the *Acinetobacter* is *Acinetobacter* sp. AK226, deposited with the National Institute of Bioscience and Human-Technology, Japan under the accession number FERM BP-2451, or *Acinetobacter* sp. AK227, deposited with the National Institute of Bioscience and Human-Technology, Japan under the accession number FERM BP-7413.

19. The method according to item 17 above, wherein the microbial strain of the *Rhodococcus* is *Rhodococcus maris* BP-479-9, deposited with the National Institute of Bioscience and Human-Technology, Japan under the accession number FERM BP-5219.

20. The method according to item 17 above, wherein the microbial strain of the *Corynebacterium* is *Corynebacterium* sp. C5, deposited with the National Institute of Bioscience and Human-Technology, Japan under the accession number FERM BP-7414, or *Corynebacterium nitrilophilus*, deposited with the American Type Culture Collection, U.S.A under the accession number ATCC 21419.

21. The method according to item 17 above, wherein the microbial strain of the *Alcaligenes* is *Alcaligenes faecalis* IFO 13111, deposited with the National Institute of Bioscience and Human-Technology, Japan under the accession number FERM BP-4750.

22. The method according to item 17 above, wherein the microbial strain of the *Mycobacterium* is *Mycobacterium* sp. AC777, deposited with the National Institute of Bioscience and Human-Technology, Japan under the accession number FERM BP-2352.

23. The method according to item 17 above, wherein the microbial strain of the *Rhodopseudomonas* is *Rhodopseudomonas spheroides*, deposited with the American Type Culture Collection, U.S.A under the accession number ATCC 11167.

24. The method according to item 17 above, wherein the microbial strain of the Candida is *Candida tropicalis*, deposited with the American Type Culture Collection, U.S.A under the accession number ATCC 20311.

25. The method according to any one of items 1 to 24 above, wherein the isolation of the glycine from the hydrolysis reaction system is conducted while recovering the by-produced ammonia separately from the recovery of glycine.

26. The method according to item 25 above, wherein the glycine and the ammonia are separately recovered by at least one operation selected from the group consisting of distillation, reactive distillation, entrainment by inert gas, ion exchange, extraction, reprecipitation using a poor solvent, and crystal-deposition by concentration or cooling.

27. The method according to item 26 above, wherein the ammonia is recovered by distillation, reactive distillation or entrainment by an inert gas, and the glycine is recovered by subjecting a liquid remaining after the recovery of the ammonia to crystal-deposition by concentration or cooling.

28. The method according to any one of items 1 to 27 above, which comprises:

(1) reacting hydrogen cyanide with formaldehyde in an aqueous medium in the presence of an alkali catalyst in a closed reaction system to obtain glycolonitrile in the form of an aqueous solution thereof, (2) adding ammonia to the aqueous solution of glycolonitrile to effect a reaction between the glycolonitrile and the ammonia, to thereby obtain glycinonitrile in the form of an aqueous solution thereof while producing water, (3) separating most of the ammonia and a part of the water from the obtained aqueous solution of glycinonitrile by distillation to thereby obtain a hydrolysis reaction system containing the glycinonitrile in the form of an aqueous solution thereof and the ammonia remaining unseparated, wherein the separated ammonia is recovered for recycle thereof to step (2), (4) subjecting the hydrolysis reaction system to a hydrolysis reaction under the action of a microbial enzyme produced by a microorganism added in the hydrolysis reaction system which is in a closed system, thereby converting the glycinonitrile to glycine while by-producing ammonia, (5) separating the microorganism and the microbial enzyme by at least one operation selected from the group consisting of centrifugal filtration and membrane filtration, wherein the microorganism and the microbial enzyme are recovered for recycle thereof to step (4), (6) separating a part of organic impurity compounds inhibiting the microbial enzyme which compounds are by-produced in steps (1) to (5) by at least one operation selected from the group consisting of membrane filtration and adsorbent-separation, (7) separating by distillation the ammonia by-produced in step (4) and an excess amount of water which remains in the hydrolysis reaction system after step (4), wherein the separated ammonia is recovered for recycle thereof to step (2), (8) after or simultaneously with step (7), separating the glycine by crystal-deposition, and (9) drying the crystals of the glycine.

29. A method for producing glycine, comprising providing glycinonitrile in the form of an aqueous solution thereof, subjecting the aqueous solution of glycinonitrile to a hydrolysis reaction, thereby converting the glycinonitrile to glycine while by-producing ammonia, and isolating the glycine from the hydrolysis reaction system, wherein the hydrolysis of glycinonitrile is conducted in the presence of ammonia.

30. The method according to item 29 above, wherein the amount of the ammonia is from 0.001 to 5 mol, relative to 1 mole of the glycinonitrile.

31. A method for producing glycine, comprising providing glycinonitrile in the form of an aqueous solution thereof, subjecting the aqueous solution of glycinonitrile to a hydrolysis reaction, thereby converting the glycinonitrile to glycine while by-producing ammonia, and isolating the glycine from the hydrolysis reaction system, wherein the isolation of the glycine from the hydrolysis reaction system is conducted while recovering the by-produced ammonia separately from the recovery of glycine in the absence of a base and an acid.

32. The method according to item 31 above, wherein the glycine and ammonia are separately recovered by at least one operation selected from the group consisting of distillation, reactive distillation, entrainment by an inert gas, ion exchange, extraction, reprecipitation using a poor solvent, and crystal-deposition by concentration or cooling.

33. The method according to item 32 above, wherein the ammonia is recovered by distillation, reactive distillation or entrainment by an inert gas, and the glycine is recovered by subjecting a liquid remaining after the recovery of the ammonia to crystal-deposition by concentration or cooling.

Hereinbelow, the present invention will be described in detail.

In the present invention, it is preferred that glycinonitrile is synthesized from hydrogen cyanide, formaldehyde and ammonia. Glycinonitrile can be synthesized by the conventional methods. Specifically, glycinonitrile can be synthesized by, for example, a method in which glycolonitrile (hydroxyacetonitrile) is synthesized from hydrogen cyanide and formaldehyde and then ammonia is added to and reacted with the glycolonitrile to thereby obtain glycinonitrile; or a method in which glycinonitrile is directly synthesized from hydrogen cyanide, formaldehyde and ammonia.

The hydrolysis reaction system used in the present invention comprises glycolonitrile, glycinonitrile, glycine, ammonia, water, a catalyst, an organic impurity compound inhibiting a microbial enzyme and the like.

The organic impurity compound inhibiting the microbial enzyme which is contained in the hydrolysis reaction system is either a compound which inhibits a microbial enzyme reversibly or a compound which inhibits a microbial enzyme irreversibly to deactivate the enzyme and make it impossible to reuse the microbial enzyme. Such organic impurity compound has a molecular weight of 95 or more and contains at least one member selected from the group consisting of a nitrile group, a carboxyl group, an amide group, an amino group, a hydroxyl group and a trimethyleneamine structure. For example, the organic impurity compound may be any of the following substances: raw materials used for producing glycine; additives contained in a catalyst and the like; and the impurities contained in the raw materials. In addition, the organic impurity compound may be any of the following substances: the compounds which are by-produced during the synthesis of glycinonitrile from hydrogen cyanide, formaldehyde and ammonia; and the compounds which are by-produced during the hydrolysis of glycinonitrile (aminoacetonitrile) into glycine and ammonia. Further, the organic impurity compound may be any of the following substances: the compounds which are by-produced during the production of the microbial enzyme having the activity to hydrolyze a nitrile group; and the by-products which are recycled from the step of separating and purifying glycine.

Specific examples of organic impurity compounds, which are contained in the hydrolysis reaction system used in the present invention, include at least one compound selected from the group consisting of the following compounds (A) to (F).

(A) A compound represented by the following formula (2):

$$NH_{3-n}(CH_2Y^1)_n \tag{2}$$

wherein each $Y^1$ independently represents a nitrile group, a carboxyl group or an amide group; and n represents an integer of 2 or 3.

Compounds represented by formula (2) above are a condensation compound containing an imine (—NH—) structure or a nitrilo (—N≡) structure and a compound formed by hydrolysis thereof. As examples of such condensation compounds, there can be mentioned iminodiacetonitrile and nitrilotriacetonitrile which are known to be formed by the condensation reaction between glycolonitrile and glycinonitrile. Examples of compounds formed by the hydrolysis of the nitrile group of such condensation compounds include iminodiacetic acid, cyanomethylaminoacetic acid, iminodiacetoamide, cyanomethylaminoacetoamide, carbamoylmethylaminoacetic acid, nitrilotriacetic acid, N-(cyanomethyl)iminodiacetic acid, N,N-bis(cyanomethyl)aminoacetic acid, N-(carbamoylmethyl)iminodiacetic acid, N,N-bis(carbamoylmethyl)aminoacetic acid, nitrilotriacetoamide, N-(cyanomethyl)iminodiacetoamide, N,N-bis(cyanomethyl)aminoacetoamide and the like.

(B) At least one compound selected from the group consisting of the following compounds (a) and (b):

(a) a compound represented by the following formula (3):

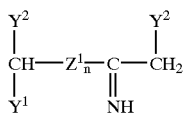

(3)

wherein:

$Y^1$ represents a nitrile group, a carboxyl group or an amide group;

each $Y^2$ independently represents an amino group or a hydroxyl group;

n represents an integer of 0 to 100; and the or each $Z^1$ is independently represented by the following formula (4) or (5):

(4)

(5)

wherein each $Y^2$ independently represents an amino group or a hydroxyl group, and (b) a compound represented by the following formula (6) or (7):

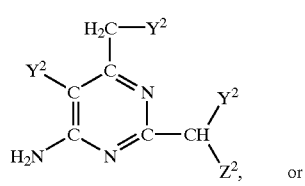

(6)

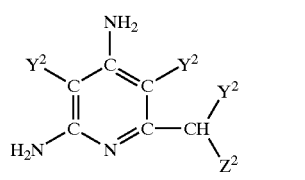

(7)

wherein each $Y^2$ independently represents an amino group or a hydroxyl group; and each $Z^2$ is independently represented by the following formula (8) or (9):

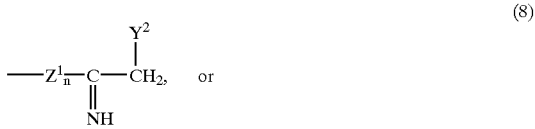

(8)

(9)

wherein:

$Y^2$ represents an amino group or a hydroxyl group;

the or each $Z^1$ is as defined for formula (3); and n represents an integer of 0 to 100.

Compounds represented by formula (3) above are an addition polymerization compound and a compound formed by the hydrolysis of the nitrile group of the addition polymerization compound. Compounds represented by formula (6) are an addition cyclization compound having a pyrimidine skeleton, which is formed by the cyclization of the above-mentioned addition polymerization compound, and a compound formed by the hydrolysis of the nitrile group of such an addition cyclization compound. Compounds represented by formula (7) are an addition cyclization compound having a pyridine skeleton, which is formed by the cyclization of the above-mentioned addition polymerization compound, and a compound formed by the hydrolysis of the nitrile group of such an addition cyclization compound. As exemplified by the addition reaction of phenylacetonitrile, which is described in "Jikken Kagaku Kouza (Lectures on Experimental Chemistry)", 1st ed., Volume 18-2, page 347, published by Japanese Chemical Society, Japan, such addition compounds are known to be produced by a mechanism by which a cyanomethyl group undergoes an addition dimerization or addition trimerization, which is optionally followed by cyclization or polymerization.

Examples of addition dimers represented by formula (3) above include compounds obtained by an addition reaction between glycolonitrile and glycinonitrile, namely 1,3-diamino-2-imino-butylonitrile, 1,3-dihydroxy-2-imino-butylonitrile, 1-amino-2-imino-3-hydroxybutylonitrile and 3-amino-2-imino-1-hydroxybutylonitrile. Examples of compounds formed by the hydrolysis of the nitrile group of the above-mentioned compounds include 1,3-diamino-2-imino-butylic acid, 1,3-dihydroxy-2-imino-butylic acid, 1-amino-2-imino-3-hydroxybutylic acid, 3-amino-2-imino-1-hydroxybutylic acid, 1,3-diamino-2-imino-butylamide, 1,3-dihydroxy-2-imino-butylamide, 1-amino-2-imino-3-hydroxybutylamide, 3-amino-2-imino-1-hydroxybutylamide and the like.

As examples of addition trimers which are represented by formula (3) above and which contain a structure represented by formula (4) above, i.e., a structure wherein a nitrile group is addition-bonded to a methylene group, there can be mentioned 1,3,5-triamino-2,4-diiminohexanenitrile, 1,3-diamino-2,4-diimino-5-hydroxyhexanenitrile, 1,5-diamino-2,4-diimino-3-hydroxyhexanenitrile, 3,5-diamino-2,4-diimino-1-hydroxyhexanenitrile, 1-amino-2,4-diimino-3,5-dihydroxyhexanenitrile, 3-amino-2,4-diimino-1,5-dihydroxyhexanenitrile, 5-amino-2,4-diimino-1,3-dihydroxyhexanenitrile, 2,4-diimino-1,3,5-trihydroxyhexanenitrile and the like. Examples of compounds formed by the hydrolysis of the nitrile group of the above-mentioned compounds include 1,3,5-triamino-2,4-diiminohexanonic acid, 1,3-diamino-2,4-diimino-5-hydroxyhexanonic acid, 1,5-diamino-2,4-diimino-3-hydroxyhexanonic acid, 3,5-diamino-2,4-diimino-1- hydroxyhexanonic acid, 1-amino-2,4-diimino-3,5-dihydroxyhexanonic acid, 3-amino-2,4-diimino-1,5-dihydroxyhexanonic acid, 5-amino-2,4-diimino-1,3-dihydroxyhexanonic acid, 2,4-diimino-1,3,5-trihydroxyhexanonic acid, 1,3,5-triamino-2,4-diiminohexaneamide, 1,3-diamino-2,4-diimino-5-hydroxyhexaneamide, 1,5-diamino-2,4-diimino-3-hydroxyhexaneamide, 3,5-diamino-2,4-diimino-1-hydroxyhexaneamide, 1-amino-2,4-diimino-3,5-dihydroxyhexaneamide, 3-amino-2,4-diimino-1,5-dihydroxyhexaneamide, 5-amino-2,4-diimino-1,3-dihydroxyhexaneamide, 2,4-diimino-1,3,5-trihydroxyhexaneamide and the like.

As examples of addition trimers which are represented by formula (3) above and which contain a structure represented by formula (5) above, i.e., a structure wherein a nitrile group is addition-bonded to an imino group, there can be mentioned 2,4-diamino-3-(2-amino-1-iminoethylimino)butylonitrile, 2-amino-4-hydroxy-3-(2-amino-1-iminoethylimino)butylonitrile, 4-amino-2-hydroxy-3-(2-amino-1-iminoethylimino)butylonitrile, 2,4-dihydroxy-3-(2-amino-1-iminoethylimino)butylonitrile, 2,4-diamino-3-(2-hydroxy-1-iminoethylimino)butylonitrile, 2-amino-4-hydroxy-3-(2-hydroxy-1-iminoethylimino)butylonitrile, 4-amino-2-hydroxy-3-(2-hydroxy-1-iminoethylimino)butylonitrile, 2,4-dihydroxy-3-(2-hydroxy-1-iminoethylimino)butylonitrile and the like. Examples of compounds formed by the hydrolysis of the nitrile group of the above-mentioned compounds include 2,4-diamino-3-(2-amino-1-iminoethylimino)butylic acid, 2-amino-4-hydroxy-3-(2-amino-1-iminoethylimino)butylic acid, 4-amino-2-hydroxy-3-(2-amino-1-iminoethylimino)butylic acid, 2,4-dihydroxy-3-(2-amino-1-iminoethylimino)butylic acid, 2,4-diamino-3-(2-hydroxy-1-iminoethylimino)butylic acid, 2-amino-4-hydroxy-3-(2-hydroxy-1-iminoethylimino)butylic acid, 4-amino-2-hydroxy-3-(2-hydroxy-1-iminoethylimino)butylic acid, 2,4-dihydroxy-3-(2-hydroxy-1-iminoethylimino)butylic acid, 2,4-diamino-3-(2-amino-1-iminoethylimino)butylamide, 2-amino-4-hydroxy-3-(2-amino-1-iminoethylimino)butylamide, 4-amino-2-hydroxy-3-(2-amino-1-iminoethylimino)butylamide, 2,4-dihydroxy-3-(2-amino-1-iminoethylimino)butylamide, 2,4-diamino-3-(2-hydroxy-1-iminoethylimino)butylamide, 2-amino-4-hydroxy-3-(2-hydroxy-1-iminoethylimino)butylamide, 4-amino-2-hydroxy-3-(2-hydroxy-1-iminoethylimino)butylamide, 2,4-dihydroxy-3-(2-hydroxy-1-iminoethylimino)butylamide and the like.

Examples of compounds represented by formula (3) above also include addition polymerization compounds in which the nitrile group of glycinonitrile or glycolonitrile is addition-bonded to either the methyl group or the imino group of the above-mentioned compounds. Such compounds represented by formula (3) above can have a random copolymer configuration wherein the structural unit represented by formula (4) above and the structural unit represented by formula (5) above are alternately arranged in the molecule, or a block copolymer configuration wherein the molecule contains at least two different polymer blocks, each of which independently contains at least one of the structural units represented by formulae (4) and (5).

As examples of addition cyclization compounds represented by formula (6) above which have a pyrimidine skeleton formed by the cyclization of a terminal having a nitrile group, there can be mentioned 4,5-diamino-2,6-bis(aminomethyl)pyrimidine, 4-amino-5-hydroxy-2,6-bis(aminomethyl)pyrimidine, 5-amino-4-hydroxy-2,6-bis(aminomethyl)pyrimidine, 4,5-diamino-2-aminomethyl-6-hydroxymethylpyrimidine, 4-amino-5-hydroxy-2-aminomethyl-6-hydroxypyrimidine, 5-amino-4-hydroxy-2-aminomethyl-6-hydroxypyrimidine, 4,5-diamino-6-aminomethyl-2-hydroxymethylpyrimidine, 4-amino-5-hydroxy-6-aminomethyl-2-hydroxypyrimidine, 5-amino-4-hydroxy-6-aminomethyl-2-hydroxypyrimidine, 4,5-diamino-2,6-bis(hydroxymethyl)pyrimidine, 4-amino-5-hydroxy-2,6-bis(hydroxymethyl)pyrimidine, 5-amino-4-hydroxy-2,6-bis(hydroxymethyl)pyrimidine and the like. Further examples of compounds represented by formula (6) above include addition cyclization compounds formed by a reaction in which a nitrile group is addition-bonded to a methylene group at the 1-position of any of the above-mentioned compounds, and the resultant compound is substituted with the substituent represented by formula (8) or (9) above. Such compounds represented by formula (6) above can have a random copolymer configuration wherein the structural unit represented by formula (4) above and the structural unit represented by formula (5) above are alternately arranged in the molecule, or a block copolymer configuration wherein the molecule contains at least two different polymer blocks, each of which independently contains at least one of the structural units represented by formulae (4) and (5). In addition, the compounds formed by the hydrolysis of the nitrile group of the above-mentioned addition cyclization compounds can also be mentioned as examples of compounds represented by formula (6).

As examples of addition cyclization compounds represented by formula (7) above which have a pyridine skeleton formed by the cyclization of a terminal having a nitrile group, there can be mentioned 2,3,4,5-tetra-amino-6-aminomethylpyridine, 2,3,4-triamino-5-hydroxy-6-aminomethylpyridine, 2,4,5-triamino-3-hydroxy-6-aminomethylpyridine, 2,4,5-triamino-3,5-dihydroxy-6-aminomethylpyridine, 2,3,4,5-tetramino-6-hydroxymethylpyridine, 2,3,4-triamino-5-hydroxy-6-hydroxymethylpyridine, 2,4,5-triamino-3-hydroxy-6-hydroxymethylpyridine and 2,4,5-triamino-3,5-dihydroxy-6-hydroxymethylpyridine. Further examples of compounds represented by formula (7) above include addition cyclization compounds formed by a reaction in which a nitrile group is addition-bonded to a methylene group at the 6-position of any of the above-mentioned compounds, and the resultant compound is substituted with the substituent represented by formula (8) or (9) above. Such compounds represented by formula (7) above can have a random copolymer configuration wherein the structural unit represented by formula (4) above and the structural unit represented by formula (5) above are alternately arranged in the molecule, or a block copolymer configuration wherein the molecule contains at least two different polymer blocks, each of which independently contains at least one of the structural units represented by formulae (4) and (5). In addition, the compounds formed by the hydrolysis of the nitrile group of the above-mentioned addition cyclization compounds can also be mentioned as examples of compounds represented by formula (7).

(C) At least one compound selected from the group consisting of the following compounds (c) and (d):

(c) a compound represented by the following formula (10) or (11):

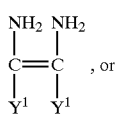

(10)

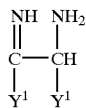

(11)

wherein each $Y^1$ independently represents a nitrile group, a carboxyl group or an amide group, and (d) a compound represented by the following formula (12):

$$(HCN)_n \qquad (12)$$

wherein n represents an integer of 4 to 200.

Compounds represented by formula (10) or (11) above are a tetramer of hydrogen cyanide and a compound formed by the hydrolysis of the nitrile group of the tetramer. Compounds represented by formula (12) above are polymers of hydrogen cyanide.

Examples of compounds represented by formula (10) or (11) above (i.e., tetramers of hydrogen cyanide) include diaminomaleonitrile and a tautomer thereof, namely aminoiminosuccinonitrile. Examples of compounds formed by the hydrolysis of the nitrile group of the tetramers of hydrogen cyanide include diaminomaleic acid, 2,3-diamino-3-cyanoacrylic acid, 2,3-diamino-3-cyanoacrylamide, 2,3-diamino-3-carbamoylacrylic acid, 2,3-diamino-3-carbamoylacrylamide, aminoiminosuccinonic acid, 2-amino-3-imino-3-carbamoylpropionamide, 2-amino-3-imino-3-cyanopropionic acid, 2-amino-3-imino-3-cyanopropionamide, 2-amino-3-imino-3-carbamoylpropionic acid, 3-amino-2-imino-3-cyanopropionic acid, 3-amino-2-imino-3-cyanopropionamide and 3-amino-2-imino-3-carbonylpropionic acid.

Examples of hydrogen cyanide polymers represented by formula (12) above include the following compounds. When n=4, in addition to the compounds represented by formula (10) or (11) above, there can be mentioned 3-amino-2,4-diiminobutylic acid; when n=5, there can be mentioned 3-amino-3-cyano-2,4-diiminobutylic acid and 3-amino-2,4,5-triiminohepthanoic acid; when n=6, there can be mentioned 3,4-diamino-3,4-dicyano-2-iminobutylic acid, 3-amino-3-cyano-2,4,5-triiminohepthanoic acid and the like. Further examples of hydrogen cyanide polymers represented by formula (12) include hydrogen cyanide polymers in which n is 7 or more.

(D) A compound having in a molecule thereof at least one skeleton selected from the group consisting of the following skeletons (e) and (f):

(e) a skeleton represented by the following formula (13):

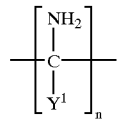

(13)

wherein each $Y^1$ independently represents a nitrile group, a carboxyl group or an amide group; and n represents an integer of 2 to 120, and (f) a skeleton represented by the following formula (14) or (15):

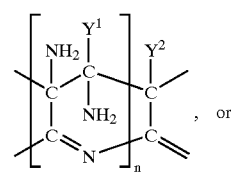

(14)

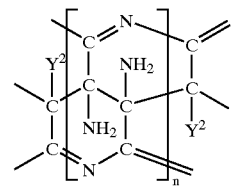

(15)

wherein:
  each $Y^1$ independently represents a nitrile group, a carboxyl group or an amide group;
  each $Y^2$ independently represents an amino group or a hydroxyl group; and
  n represents an integer of 1 to 70.

Examples of compounds having in a molecule thereof a skeleton represented by formula (13) above include a polymer of hydrogen cyanide and a polymer formed by the hydrolysis of the nitrile group of the hydrogen cyanide polymer. As a specific example of such a hydrogen cyanide polymer, there can be mentioned a polymer which has at least one structure selected from the group consisting of an aminocyanomethylene structure, an aminocarbamoylmethylene structure and an aminocarboxymethylene structure and which has 2 or more recurring units. The hydrogen cyanide polymer mentioned above may be a compound which exhibits a peak between 70 ppm and 90 ppm in a $^{13}$C-NMR spectrum as measured in heavy water, wherein the peak is ascribed to a methylene structure.

Examples of compounds having in a molecule thereof a skeleton represented by formula (14) or (15) above include a polycyclic compound and a compound formed by the hydrolysis of the nitrile group of the polycyclic compound. As specific examples of such compounds, there can be mentioned a polycyclic compound in which the 5-position and 6-position of a 6-membered ring having 3,4,4,5-tetramino-4-(cyano, carboxy or carbamoyl)-3,4,5,6-tetrahydropyridine skeleton are respectively the 2-position and 3-position of an adjacent 6-membered ring, and a polycyclic compound in which the 6-position, 7-position, 8-position and 9-position of a 3,7,9,10-tetramino-3,4,6,7,9,10-hexahydropyridino[2,3-e] pyridine skeleton are respectively the 5-position, 10-position, 4-position and 3-position of an adjacent pyridine skeleton. Such a polycyclic compound may be a compound which exhibits a peak between 60 ppm and 80 ppm in a $^{13}$C-NMR spectrum as measured in heavy water, wherein the peak is ascribed to a methylene structure. Such a polycyclic compound may be a compound which exhibits absorption maximums at 380 nm and 460 nm in an ultraviolet-visible absorption spectrum.

The mechanism of the production of the above-mentioned hydrogen cyanide polymers and the like is described in "Kogyo Kagaku Zasshi (Journal of Industrial Chemistry)", Volume 70, page 54 (1967) which is published by Japanese Chemical Society, Japan.

(E) A compound having in a molecule thereof at least one skeleton selected from the group consisting of the following skeletons (g) and (h):

(g) a skeleton represented by the following formula (16):

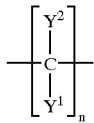

(16)

wherein:
each $Y^1$ independently represents a nitrile group, a carboxyl group or an amide group;
each $Y^2$ independently represents an amino group or a hydroxyl group;
and n represents an integer of 2 to 120, and (h) a skeleton represented by the following formula (17) or (18):

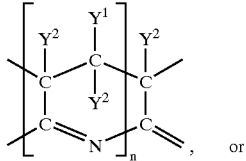

(17)

, or

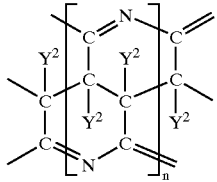

(18)

wherein:
each $Y^1$ independently represents a nitrile group, a carboxyl group or an amide group;
each $Y^2$ independently represents an amino group or a hydroxyl group; and
n represents an integer of 1 to 70.

The compounds having in a molecule thereof a skeleton represented by formula (16) above are a compound formed by oxidative polymerization (i.e., an oxidative polymerization product) and a compound formed by the hydrolysis of the nitrile group of the oxidative polymerization product. These compounds are known to be produced by an oxidative coupling reaction of methylene groups. Examples of such compounds include 2,3-diaminosuccinonitrile and 2-amino-3-hydroxysuccinonitrile (which are formed by oxidative coupling of glycolonitrile and glycinonitrile); and compounds formed by the hydrolysis of the above-mentioned compounds, such as 2,3-diaminosuccinonic acid, 2,3-diamino-3-carbamoylpropionamide, 2,3-diamino-3-cyanopropionic acid, 2,3-diamino-3-carbamoylpropionic acid, 2,3-diamino-3-cyanopropionamide, 2-amino-3-hydroxy-3-cyanopropionic acid, 2-amino-3-hydroxy-3-carbamoylpropionic acid, 2-amino-3-hydroxy-3-cyanopropionamide, 3-amino-2-hydroxy-3-cyanopropionic acid, 3-amino-2-hydroxy-3-carbamoylpropionic acid and 3-amino-2-hydroxy-3-cyanopropionamide. Further examples of compounds (E) include oxidative polymerization products which have a structure wherein a methylene compound is coupled to any of the above-mentioned compounds which have in a molecule thereof a skeleton represented by formula (16), and also include the compounds formed by the hydrolysis of the nitrile group of such oxidative polymerization products. A specific example of such a compound is a compound which has at least one structure selected from the group consisting of an aminocyanomethylene structure, an aminocarbamoylmethylene structure, an aminocarboxymethylene structure, a hydroxycyanomethylene structure, a hydroxycarbamoylmethylene structure and a hydroxyaminocarboxymethylene structure, and which has 2 or more recurring units. Such an oxidative polymerization product mentioned above may be a compound which exhibits a peak between 70 ppm and 90 ppm in a $^{13}$C-NMR spectrum as measured in heavy water, wherein the peak is ascribed to a methylene structure.

A compound having in a molecule thereof a skeleton represented by formula (17) or (18) is formed by an addition cyclization of the cyano group of the above-mentioned oxidative polymerization product. Such compounds are a polycyclic compound having in a molecule thereof a skeleton represented by formula (17) or (18) above and a compound formed by the hydrolysis of the nitrile group of the polycyclic compound. As examples of such compounds, there can be mentioned a polycyclic compound in which the 5-position and 6-position of a 6-membered ring having a 3,4,4,5-(amino and/or hydroxy)-4-(cyano, carboxy or carbamoyl)-3,4,5,6-tetrahydropyridine skeleton are respectively the 2-position and 3-position of an adjacent 6-membered ring, and a polycyclic compound in which the 6-position, 7-position, 8-position and 9-position of a 3,7,9,10-(amino and/or hydroxy)-3,4,6,7,9,10-hexahydropyridino[2,3-e] pyridine skeleton are respectively the 5-position, 10-position, 4-position and 3-position of an adjacent pyridine skeleton. Such a polycyclic compound may be a compound which exhibits a peak between 60 ppm and 80 ppm in a $^{13}$C-NMR spectrum as measured in heavy water, wherein the peak is ascribed to a methylene structure. In addition, such a polycyclic compound may be a compound which exhibits absorption maximums between 340 nm and 380 nm and between 440 nm and 480 nm in an ultraviolet-visible absorption spectrum.

(F) Hexamethylenetetramine and a compound having a trimethyleneamine structure which has a skeleton represented by the following formula (1):

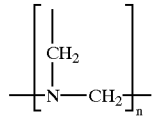

(1)

wherein n represents an integer of 1 to 150.

Such compounds are known to be produced by the condensation of formaldehyde and ammonia. Examples of compounds having a structure represented by formula (1) above include the following compounds. When n=1, there can be mentioned N-aminomethyl-hexahydro-1,3,5-triazine; when n=2, there can be mentioned N,N'-bisaminomethyl-hexahydro-1,3,5-triazine, pentamethylenetetramine and hexamethylenepentamine; when n=3, there can be mentioned N,N',N''-trisaminomethylhexahydro-1,3,5-triazine; and when n=4, there can be mentioned hexamethylenetetramine and heptamethylene pentamine.

As explained above in detail, examples of organic impurity compounds, which are contained in the hydrolysis reaction system used in the present invention, include a compound formed by a condensation reaction between a hydroxyl group and an amino group, a compound formed by an addition reaction between a nitrile group and an activated methylene group, a compound formed by a cyclization reaction between a nitrile group and an activated methylene group, a compound formed by an oxidation reaction of a methylene group, a compound formed by a cyclization reaction of a methylene group, and a compound formed by the hydrolysis of a nitrile group of the above-mentioned compounds. Further examples of organic impurity compounds include compounds formed by a combination of the above-mentioned reactions, namely the following compounds (I) to (V):

(I) a compound formed by a condensation reaction between an amino group of either a compound represented by formula (3), (6), (7), (10) or (11) or a skeleton represented by any one of formulae (13) to (18) and a hydroxyl group of either a compound represented by formula (3), (6) or (7) or a skeleton represented by any one of formulae (14) to (18);

(II) a compound formed by an addition reaction of a nitrile group of either a compound represented by any one of formulae (2), (3) and (10) to (12) or a skeleton represented by formula (13), (14), (16) or (17);

(III) a compound formed by an addition reaction between a nitrile group of either a compound represented by any one of formulae (2), (3) and (10) to (12) or a skeleton represented by formula (13), (14), (16) or (17) and an imino group of a compound represented by formula (3), (6), (7) or (11);

(IV) a compound formed by an addition reaction between a nitrile group of either a compound represented by any one of formulae (2), (3) and (10) to (12) or a skeleton represented by formula (13), (14), (16) or (17) and a methylene group of a compound represented by any one of formulae (1) to (3), (6) and (7); and (V) a compound formed by an oxidative coupling of a methylene group of one or more of the compounds represented by any one of formulae (1) to (3), (6) and (7).

Such a compound may be a compound which exhibits a peak between 53 ppm and 100 ppm in a $^{13}$C-NMR spectrum as measured in heavy water. Further, since a compound produced by a cyclization reaction is discolored, a cyclization compound as an organic impurity compound may be a compound which exhibits absorption maximums between 340 nm and 380 nm and between 440 nm and 480 nm in an ultraviolet-visible absorption spectrum.

The organic impurity compound contained in the hydrolysis reaction system used in the present invention is a polyfunctional compound having a molecular weight of 95 or more and such a compound markedly lowers the activity of a microbial enzyme. In the present invention, glycine is produced under conditions wherein the content of the organic impurity compound having a molecular weight of 95 or more, preferably 130 or more, in the hydrolysis reaction system is maintained at a level of 10% by weight or less, preferably 5% by weight or less, more preferably 1% by weight or less, based on the weight of the hydrolysis reaction system, so as to improve the activity of the microbial enzyme.

With respect to the method for maintaining the content of the organic impurity compound in the hydrolysis reaction system at a level of 10% by weight or less, based on the weight of the hydrolysis reaction system, there can be mentioned a method wherein the amount of oxygen dissolved in the hydrolysis reaction system is suppressed to 5 ppm by weight or less, based on the weight of the hydrolysis reaction system. The amount of oxygen dissolved in the hydrolysis reaction system under atmospheric pressure is generally 8 ppm to 10 ppm by weight. When the amount of oxygen dissolved in the hydrolysis reaction system is suppressed to 5 ppm by weight or less, the formation of the by-products is lowered. For suppressing the inhibition of the hydrolytic activity of the microbial enzyme and the like, it is preferred that the amount of oxygen dissolved in the hydrolysis reaction system is 0.5 ppm by weight or less, more advantageously 0.05 ppm by weight or less, based on the weight of the hydrolysis reaction system.

In the present invention, as a method for suppressing the amount of oxygen dissolved in the hydrolysis reaction system, a method can be employed in which the hydrolysis is conducted using a closed reaction system which is sealed off from the air, a reaction system which is pressurized with an inert gas, a reaction system through which an inert gas is flowed, or a reaction system which is under a pressure of less than atmospheric pressure. As examples of inert gases, there can be mentioned noble gases, such as helium gas and argon gas; natural gases, such as methane gas, ethane gas and propane gas; low boiling point ethers, such as diethyl ether; and nitrogen gas. These gasses can be used individually or in combination. From the viewpoint of safety and the like, nitrogen gas is preferred. In the case wherein a closed reaction system is used, sealing off of the reaction system from the air can be more effectively performed by pressurizing the reaction system with an inert gas. With respect to the pressure level to which the reaction system should be pressurized, there is no particular limitation. However, in view of the pressure resistance of the microbial enzyme used, it is preferred that the pressure of the pressurized reaction system is in the range of from superatmospheric pressure to 1.0 MPa, more advantageously superatmospheric pressure to 0.5 MPa. On the other hand, when a reaction system which is under a pressure of less than atmospheric pressure is used, the pressure of the reaction system can be in the range of from more than 0.7 kPa (0.7 kPa is the vapor pressure of water at 0° C.) to less than atmospheric pressure, preferably from more than 4.0 kPa to less than atmospheric pressure.

In the present invention, for suppressing the amount of oxygen dissolved in the hydrolysis reaction system, it is necessary to not only seal off the reaction system from the air, but also remove oxygen which is dissolved in the raw materials and the like. Various conventional methods can be employed for removing oxygen from the reaction system. For example, there can be mentioned a distillation deaeration method in which oxygen dissolved in the reaction system is removed by distillation; an inert gas flow treatment method in which an inert gas is flowed through the reaction system to thereby replace oxygen dissolved in the system by an inert gas; and a reductive compound addition treatment method in which a reductive compound is added to the reaction system to thereby consume oxygen by reduction. Examples of reductive compounds which can be used for the reductive compound addition treatment include reductive biochemical compounds, compounds of formic acid and compounds of sulfurous acid. With respect to the reductive biochemical compounds which can be used for the reductive compound addition treatment, there is no particular limitation. For example, there can be used L-ascorbic acid; L-ascorbic acid esters, such as L-ascorbic acid stearic acid ester; salts, such as sodium L-ascorbate; glutathione; L-cysteine; cysteine salts, such as L-cysteine hydrochloride monohydrate; cysteine esters, such as L-cysteine ethyl ester chloride and L-cysteine methyl ester chloride; and N-substituted cysteines, such as N-acetyl-L-cysteine. Among these compounds, L-ascorbic acid is preferred. The amount of the reductive biochemical compound added to the reaction system varies depending on the amount of oxygen dissolved in the system; however, from the viewpoint of the stabilization of glycinonitrile, the reductive biochemical compound is added in an amount of 0.001 to 5 mol %, preferably 0.01 to 2 mol %, based on the molar amount of glycinonitrile. With respect to the reductive compounds of formic acid which can be used for the reductive compound addition treatment, there is no particular limitation. For example, there can be used formic acid; formic acid salts, such as ammonium formate; and formic acid esters, such as methyl formate and ethyl formate. Among these compounds, formic acid and ammonium formate are preferred. The amount of the reductive compound of formic acid added to the reaction system varies depending on the amount of oxygen dissolved in the system; however, from the viewpoint of the stabilization of glycinonitrile, the reductive compound of formic acid is added in an amount of 0.002 to 8 mol %, preferably 0.02 to 4 mol %, based on the molar amount of glycinonitrile. With respect to the compounds of sulfurous acid which can be used for the reductive compound addition treatment, there is no particular limitation. For example, there can be used sulfur dioxide, sulfurous acid, sodium sulfite, sodium hydrogen sulfite, potassium sulfite, potassium hydrogen sulfite and ammonium sulfite. Among these compounds, ammonium sulfite is preferred. Since the compounds of sulfurous acid are electrolytes and exhibit the effect to promote the production of by-products, the compound of sulfurous acid is added to the reaction system in an amount of 0.001 to 2% by weight, preferably 0.01 to 1% by weight, wherein the amount should be selected so as to meet the below-described requirement of the total amount of the electrolytes in the reaction system.

Further, as another method for maintaining the content of the organic impurity compound in the hydrolysis reaction system at a level of 10% by weight or less, based on the weight of the hydrolysis reaction system, there can be mentioned a method wherein ammonia is used as a stabilizer for glycinonitrile. When glycinonitrile is heated, ammonia and imine compounds (such as iminodiacetonitrile) are generated and further heating causes the imine compounds to denature, resulting in the generation of black compounds. Therefore, glycinonitrile can be stabilized by using a hydrolysis reaction system having ammonia dissolved therein. The amount of ammonia to be added to the reaction system may vary depending on the reaction temperature and reaction time, but it is preferred that ammonia is used in an amount of 0.001 to 5 mol, more advantageously 0.01 to 2 mol, per mol of glycinonitrile per liter. In general, excess ammonia remains in glycinonitrile after the synthesis thereof. The excess ammonia as such can be used as a stabilizer without separating the excess ammonia from glycinonitrile.

In addition, as a further method for maintaining the content of the organic impurity compound in the hydrolysis reaction system at a level of 10% by weight or less, based on the weight of the hydrolysis reaction system, there can be mentioned a method wherein the amount of an electrolyte in the reaction system is maintained at a level of 2% by weight or less, based on the weight of the glycinonitrile. Electrolytes are known to promote the production of by-products from nitrile compounds. Examples of electrolytes used in the present invention include not only alkali metal salts, alkaline earth metal salts and mixtures of two or more metal salts (such as phosphate buffers), but also alkali metal compounds and alkaline earth metal compounds (such as caustic soda) which are capable of forming glycine salts, and mineral acids (such as sulfuric acid, hydrochloric acid and nitric acid). The addition of such electrolytes to the reaction system promotes the formation of by-products from nitrile compounds, and, as one of the reasons for such promotion, it is noted that the addition of an electrolyte to an aqueous solution causes an increase in the amount of oxygen dissolved in the aqueous solution (see "Kagaku Benran (Chemistry Handbook)", revised 4th edition, page II-159, Table 8.54, published by Japanese Chemical Society, Japan). Therefore, it is preferred that before using the microbial enzyme, an electrolyte which is used as a culture medium or a buffer in the production of the microbial enzyme and which remains in the microbial enzyme is reduced to a predetermined level by washing, that the amount of an alkali catalyst contained in an aqueous glycinonitrile solution is decreased, and that the amount of a phosphate buffer added to a reaction medium liquid for adjusting the pH value thereof is suppressed to a level as low as possible. The total amount of the electrolytes contained in the hydrolysis reaction system is adjusted to 2% by weight or less, preferably 1% by weight or less, more preferably 0.5% by weight or less, based on the weight of the glycinonitrile.

The above-mentioned methods in which the amount of oxygen dissolved in the hydrolysis reaction system is suppressed, the above-mentioned method in which ammonia is dissolved into the hydrolysis reaction system, and the above-mentioned method in which the electrolyte concentration of the hydrolysis reaction system is controlled can be used in combination. It is preferred that all these methods are used in combination.

With respect to the microorganism which is used to produce the microbial enzyme used in the present invention wherein the enzyme has the activity to hydrolyze a nitrile group, there is no particular limitation. For example, there can be suitably used a microorganism belonging to a genus selected from the group consisting of *Acinetobacter, Rhodococcus, Corynebacterium, Alcaligenes, Mycobacterium, Rhodopseudomonas* and *Candida*. However, the microorganism is not limited to them. Specific examples of microorganisms include the following microbial strains (1) to (9):

(1) *Acinetobacter* sp. AK226 (see Examined Japanese Patent Application Publication Specification No. Sho 63-2596). deposited with the National Institute of Bioscience and Human-Technology, Japan (1-3, Higashi 1-chome, Tsukuba-shi, Ibaraki-ken, Japan (Postal Code No. 305-0046)) on May 28, 1985 (original deposit date) under the accession number FERM BP-2451;

(2) *Acinetobacter* sp. AK227 (see Examined Japanese Patent Application Publication Specification No. Sho 63-2596), deposited with the National Institute of Bioscience and Human-Technology, Japan (1-3, Higashi 1-chome, Tsukuba-shi, Ibaraki-ken, Japan (Postal Code No. 305-0046)) on May 28, 1985 (original deposit date) under the accession number FERM BP-7413;

(3) *Rhodococcus maris* BP-479-9 (see Unexamined Japanese Patent Application Laid-Open Specification Nos. Hei 7-303491 and Hei 7-303496), deposited with the National Institute of Bioscience and Human-Technology, Japan (1-3, Higashi 1-chome, Tsukuba-shi, Ibaraki-ken, Japan (Postal Code No. 305-0046)) on Nov. 2, 1993 (original deposit date) under the accession number FERM BP-5219;

(4) *Corynebacterium* sp. C5 (see Examined Japanese Patent Application Publication Specification No. Hei 6-65313), deposited with the National Institute of Bioscience and Human-Technology, Japan (1-3, Higashi 1-chome, Tsukuba-shi, Ibaraki-ken, Japan (Postal Code No. 305-0046)) on Aug. 28, 1986 (original deposit date) under the accession number FERM BP-7414;

(5) *Corynebacterium nitrilophilus* (see Unexamined Japanese Patent Application Laid-Open Specification No. Hei 2-84198), deposited with the American Type Culture Collection, U.S.A. (10801 University Boulevard, Manassas Va. (Postal Code No. 20110-2209)) under the accession number ATCC 20311.

(6) *Alcaligenes faecalis* IFO 13111 (see Unexamined Japanese Patent Application Laid-Open Specification No. Hei 6-70856), deposited with the National Institute of Bioscience and Human-Technology, Japan (1-3, Higashi 1-chome, Tsukuba-shi, Ibaraki-ken, Japan (Postal Code No. 305-0046)) on Jul. 22, 1994 (original deposit date) under the accession number FERM BP-4750;

(7) *Mycobacterium* sp. AC777 (see Unexamined Japanese Patent Application Laid-Open Specification No. Hei 2-84918 and U.S. Pat. No. 5,283,193), deposited with the National Institute of Bioscience and Human-Technology, Japan (1-3, Higashi 1-chome, Tsukuba-shi, Ibaraki-ken, Japan (Postal Code No.305-0046)) on Mar. 27, 1989 (original deposit date) under the accession number FERM BP-2352;

(8) *Rhodopseudomonas spheroides* (see Unexamined Japanese Patent Application Laid-Open Specification No. Hei 6-303991), deposited with the American Type Culture Collection, U.S.A. (10801 University Boulevard, Manassas Va. (Postal Code No. 20110-2209)) under the accession number ATCC 11167; and (9) *Candida tropicalis* (see Unexamined Japanese Patent Application Laid-Open Specification No. Hei 6-303991), deposited with the American Type Culture Collection, U.S.A. (10801 University Boulevard, Manassas Va. (Postal Code No. 20110-2209)) under the accession number ATCC 20311.

The conventional culture medium can be used for culturing a microorganism which produces the microbial enzyme used in the present invention. As a carbon source, there can be used, for example, glucose, glycerin, saccharose, fractose, organic acids (such as acetic acid), a dextrin and maltose. As a nitrogen source, there can be used ammonia and salts thereof, urea, sulfuric acid salts, nitric acid salts, organic nitrogen sources (such as yeast extract, malt extract, peptone, soy oil and meat extract). In addition, inorganic nutrients, such as phosphoric acid salts, sodium, potassium, iron, magnesium, cobalt, manganese and zinc, and vitamins are appropriately selected and added to the culture medium. The microorganism is cultured aerobically at a pH value of 4 to 10, preferably 6 to 8, at 5 to 50° C., preferably 20 to 35° C. Further, enzyme inducers, such as lactam compounds (γ-lactam, δ-lactam, ε-caprolactam and the like), nitrile compounds and amide compounds, may be added to the culture medium. With respect to the microorganism used for producing the microbial enzyme used in the present invention in the case of the commercial practice of the present invention, the microorganism in original form can be used for producing the microbial enzyme, or a mutant strain derived therefrom can be used for producing the microbial enzyme. For example, a mutant strain which produces the enzyme constitutively can be obtained by inducing a spontaneous mutation using an appropriate mutagen or by genetic engineering techniques. As the microbial enzyme used in the present invention, there can be used either of the following products: the cells of a microorganism (microbial cells) which have been recovered from a culture broth, and a microbial preparation. Examples of microbial preparations include a homogenate of a microorganism, an enzyme separated from the homogenate, an immobilized microorganism, and an immobilized enzyme which is obtained by separating and extracting an enzyme from a microorganism and immobilizing the extracted enzyme on a carrier. The microbial cells can be recovered from the culture broth by a conventional method.

In the present invention, the microbial cells or microbial preparation obtained in the above-mentioned manner can be stored in the form of an aqueous microbial suspension which is prepared by suspending the microbial cells or microbial preparation in distilled water or a buffer. For decreasing the amount of wastes discarded after the reaction, it is preferred that the above-mentioned microbial suspension is prepared using distilled water, especially recycled distilled water which is obtained by a method in which, during the crystal-deposition operation and the like, distillation is performed under conditions wherein the reaction mixture is completely sealed off from the air. For improving the storage stability, a stabilizer may be added to the microbial suspension. For decreasing the amount of wastes discarded after the reaction, glycine is preferably used as the above-mentioned stabilizer.

In the present invention, by using any one of the below-mentioned methods, the hydrolysis of glycinonitrile to produce glycine can be caused to proceed quickly: a method in which the aqueous glycinonitrile solution or the ammonia-containing aqueous glycinonitrile solution (obtained in the above-mentioned manner) is added to the aqueous suspension of microbial cells or microbial preparation (obtained in the above-mentioned manner); a method in which the aqueous suspension of microbial cells or microbial preparation is added to the aqueous glycinonitrile solution; and a method in which the microbial cells or microbial preparation (obtained in the above-mentioned manner) is immobilized on a carrier, and the aqueous glycinonitrile solution is caused to flow while contacting the immobilized microbial cells or microbial preparation. In general, 0.01 to 5% by weight of the above-mentioned microbial cells or microbial preparation, in terms of the dry weight of the microorganism, and 1 to 40% by weight of glycinonitrile (enzyme substrate) are charged into a reactor and a reaction is performed at a temperature of, for example, 0 to 60° C., preferably 10 to 50° C., for 1 to 24 hours, preferably 3 to 8 hours. There may be used a reaction method wherein glycinonitrile is charged into the reactor to obtain a low concentration of glycinonitrile, and additional glycinonitrile is then gradually charged in the course of the reaction, or a reaction method wherein the reaction temperature is changed with time. When glycinonitrile is hydrolyzed into glycine and ammonia, the pH value of the reaction system becomes high, as compared to the pH value of the reaction system before initiating the hydrolysis reaction. For preventing the pH value of the reaction system from increasing in accordance with the progress of the reaction, a buffer may be added to the reaction system before initiating the reaction, or alternatively, an acid or alkali may be added to the reaction system during the reaction. However, from the viewpoint of decreasing the amount of wastes, it is preferred that a buffer, acid or alkali is not added to the hydrolysis reaction system. The hydrolysis can be conducted in an open type reactor; however, from the viewpoint of preventing the problem that the by-produced ammonia is dispersed into the air to cause environmental pollution, viewpoint of efficient recovering of ammonia, and viewpoint of efficient sealing off of the reaction system from the air, it is preferred that the hydrolysis reaction is conducted using a closed reaction system in a sealed reactor so as to cause the by-produced ammonia to be accumulated in the reactor.

The ammonia and glycine can be separately recovered by at least one operation selected from the group consisting of distillation, reactive distillation, entrainment by inert gas, ion exchange, extraction, reprecipitation using a poor solvent, and crystal-deposition by concentration or cooling. From the viewpoint of ease in the operation and of avoiding the use of an organic solvent, acid and alkali, it is preferred that first, ammonia is recovered by distillation, reactive distillation or entrainment by an inert gas, and then, a liquid remaining after the recovery of the ammonia is subjected to crystal-deposition by concentration or cooling to thereby recover glycine. As a reactor for conducting a reactive distillation, there can be used a single column tower, a multi-stage tower or a packed tower equipped with a cooler for recovering ammonia and water by cooling. It is preferred that the reactive distillation is conducted in a continuous manner or intermittent manner under a pressure which is equal to or higher than the boiling pressure of the reaction mixture, for example, 20.0 kPa or higher at 60° C., and 0.6 kPa or higher at 0° C. It is more preferred that vacuum reactive distillation is conducted under a pressure of 12.6 kPa to 1.3 kPa. When ammonia is recovered by entrainment by an inert gas, the recovery of ammonia from the reaction mixture can be performed by a method in which a reactor is used which is equipped with a blow nozzle for introducing an inert gas and a cooling trap for recovering ammonia and water from the inert gas, and ammonia is caused to be entrained by an inert gas in a continuous manner or intermittent manner under a pressure which is in the range of from a slightly superatmospheric pressure to a reduced pressure, thereby separating ammonia from the reaction mixture. Further, for promoting the separation of ammonia, vacuum reactive distillation can be performed in a flow of an inert gas. The reaction mode can be a batchwise mode or a flow reaction mode, or a combination of the two modes.

Thus, the reaction mode for the hydrolysis reaction may vary depending on the method for adding the microorganism or glycinonitrile, and the method for separating and recovering ammonia. When an aqueous suspension of microbial cells or microbial preparation is used or when ammonia is recovered by reactive distillation or entrainment by an inert gas, in general, the hydrolysis reaction can be conducted mainly by a batchwise reaction mode or a multi-stage flow reaction mode which employs a multi-stage agitation vessel. When an immobilized microorganism is used, the hydrolysis reaction can be conducted mainly by a flow reaction mode which employs a tubular reactor. The above-mentioned reaction modes may be used in combination. The reaction mode for the hydrolysis reaction is not limited to those mentioned above.

By the method of the present invention, glycinonitrile is hydrolyzed to obtain glycine in a yield of approximately 100 mol %. All of the by-produced ammonia can be accumulated in a sealed reactor in the form of an ammonium salt of glycine, wherein the glycine in the reactor is present in the form of a highly concentrated aqueous glycine solution. Alternatively, all or a most part of the by-produced ammonia can be separated from the reaction mixture simultaneously with the reaction by reactive distillation or entrainment by an inert gas and the separated ammonia can be recovered by cooling. When the microorganism contains nitrile hydratase as a microbial enzyme, glycine is hydrolyzed by nitrile hydratase to produce glycine amide in the reaction system. In this case, by adding to the reaction system a microorganism or microbial enzyme having the activity to hydrolyze glycine amide, the glycine amide can be completely converted into glycine and ammonia. Recovery of glycine from the highly concentrated aqueous glycine solution containing ammonium salts of glycine can be conducted, for example, by a method comprising separating the microorganism or microbial enzyme by centrifugal filtration and/or membrane filtration, and recovering glycine by crystal-deposition, ion exchange or reprecipitation using a poor solvent. The by-produced ammonia can be separated by evaporation together with a part of water and then recovered by distillation or extraction. A preferred embodiment of the method of the present invention for producing glycine comprises, for example, the following steps:

(1) reacting hydrogen cyanide with formaldehyde in an aqueous medium in the presence of an alkali catalyst in a closed reaction system to obtain glycolonitrile in the form of an aqueous solution thereof, (2) adding ammonia to the aqueous solution of glycolonitrile to effect a reaction between the glycolonitrile and the ammonia, to thereby obtain glycinonitrile in the form of an aqueous solution thereof while producing water, (3) separating most of the ammonia and a part of the water from the obtained aqueous solution of glycinonitrile by distillation to thereby obtain a hydrolysis reaction system containing the glycinonitrile in the form of an aqueous solution thereof and the ammonia remaining unseparated, wherein the separated ammonia is recovered for recycle thereof to step (2), (4) subjecting the hydrolysis reaction system to a hydrolysis reaction under the action of a microbial enzyme produced by a microorganism added in the hydrolysis reaction system which is in a closed system, thereby converting the glycinonitrile to glycine while by-producing ammonia, (5) separating the microorganism and the microbial enzyme by at least one operation selected from the group consisting of centrifugal filtration and membrane filtration, wherein the microorganism and the microbial enzyme are recovered for recycle thereof to step (4), (6) separating a part of organic impurity compounds inhibiting the microbial enzyme which compounds are by-produced in steps (1) to (5) by at least one operation selected from the group consisting of membrane filtration and adsorbent-separation, (7) separating by distillation the ammonia by-produced in step (4) and an excess amount of water which remains in the hydrolysis reaction system after step (4), wherein the separated ammonia is recovered for recycle thereof to step (2), (8) after or simultaneously with step (7), separating the glycine by crystal-deposition, and (9) drying the crystals of the glycine.

In another aspect of the present invention, there is provided a method for producing glycine, which comprises providing glycinonitrile in the form of an aqueous solution thereof, subjecting the aqueous solution of glycinonitrile to a hydrolysis reaction, thereby converting the glycinonitrile to glycine while by-producing ammonia, and isolating the glycine from the hydrolysis reaction system, wherein the hydrolysis of glycinonitrile is conducted in the presence of ammonia. In this method, it is preferred that the amount of the ammonia is from 0.001 to 5 mol, relative to 1 mole of the glycinonitrile. By the use of the method of the present invention, it becomes possible to stabilize glycinonitrile and produce glycine efficiently and stoichiometrically.

In a further aspect of the present invention, there is provided a method for producing glycine, which comprises subjecting an aqueous solution of glycinonitrile to a hydrolysis reaction, thereby converting the glycinonitrile to glycine while by-producing ammonia, and isolating the glycine from the hydrolysis reaction system, wherein the isolation of the glycine from the hydrolysis reaction system is conducted while recovering the by-produced ammonia separately from the recovery of glycine in the absence of a base and an acid. In this case, it is preferred that the glycine and ammonia are separately recovered by at least one operation selected from the group consisting of distillation, reactive distillation, entrainment by an inert gas, ion exchange, extraction, reprecipitation using a poor solvent, and crystal-deposition by concentration or cooling. In addition, it is preferred that the ammonia is recovered by distillation, reactive distillation or entrainment by an inert gas, and the glycine is recovered by subjecting a liquid remaining after the recovery of the ammonia to crystal-deposition by concentration or cooling. By the use of the method of the present invention, it becomes possible to recycle ammonia and decrease the burden on the environment.

BEST MODE FOR CARRYING OUT THE INVENTION

Hereinbelow, the present invention will be described in more detail with reference to the following Examples and Comparative Example, but they should not be construed as limiting the scope of the present invention.

In the Examples and Comparative Example, in order to prevent the entry of oxygen into a reaction system, all of the basic reaction operations were conducted under a nitrogen atmosphere. In addition, before adding an aqueous solution to the reaction system for the first time, oxygen dissolved in the aqueous solution was purged with nitrogen (i.e., the oxygen concentration was decreased to 0.01 ppm or less) by subjecting the aqueous solution to a nitrogen purge operation which comprises, for example, a several-time repetition of a cycle comprising pressurizing the aqueous solution with nitrogen gas and then returning the pressure to atmospheric pressure. However, it should be noted that in a commercial scale process (Example 12), water used for preparing aqueous solutions is distilled water which has been recycled from a step of concentrating glycinonitrile and from a step of concentration for the crystal-deposition of glycine, and therefore, there is no need to conduct any special operations (for removing oxygen) other than storing the aqueous solutions and the like in a nitrogen atmosphere.

In the following Examples and Comparative Example, various operations were conducted in the following manners.

(1) Evaporation and Recovery of Ammonia and Water

Evaporation and recovery of ammonia and water were conducted using a thin film distillation apparatus (manufactured and sold by Shibata Scientific Technology Inc., Japan) under a reduced pressure and at a residence time of 1 minute or less.

(2) Concentration of a Reaction Mixture

Concentration of 30 ml or less of a reaction mixture was conducted using a rotary evaporator equipped with a circulating aspirator for operating the rotary evaporator under reduced pressure (manufactured and sold by Tokyo Rikakikai Co., Ltd., Japan).

(3) Separation of a Microorganism

Separation of a microorganism after a hydrolysis reaction of glycinonitrile was conducted by centrifuging a reaction mixture at 10,000 rpm for 15 minutes using a refrigerating centrifuge (manufactured and sold by Hitachi Ltd., Japan).

(4) Removal of Proteins

In Examples 1 to 11, proteins were removed by filtration under pressure using an ultrafiltration filter for syringes (manufactured and sold by Terumo Corp., Japan). In Example 12, proteins were removed using a circulating ultrafiltration apparatus (Ultrafiltration membrane: "SIP-1013", manufactured and sold by Asahi Kasei Kabushiki Kaisha, Japan).

(5) Liquid Chromatography

Glycine, glycinonitrile, glycolonitrile, iminodiacetonitrile, iminodiacetic acid, hexamethylenetetramine, ammonia, sulfuric acid ions, sodium ions and the like were analyzed by ion pair chromatography. As an analytical instrument, use was made of a liquid chromatography apparatus (model LC-6A, an RI and a UV detector, each manufactured and sold by Shimadzu Corporation, Japan) and a column (ODS column, manufactured and sold by Tosoh Corp., Japan). In the ion pair chromatography, sodium pentanesulfonate was used as an ion pair reagent.

(6) Gel Permeation Chromatography

Glycolonitrile having a molecular weight of 55 and organic impurity compounds having a molecular weights of 4,000 or less were analyzed by gel permeation chromatography (GPC). As a gel permeation chromatography apparatus, use was made of model LC-9A (manufactured and sold by Shimadzu Corporation, Japan) and a GPC-IR, an RI and a UV detector (each manufactured and sold by Nicolet Instrument Corporation, U.S.A.). As a column, use was made of "Asahipak GS-220 NQ column" (a Showdex column manufactured and sold by Showa Denko K.K., Japan).

(7) Analysis of a Discolored Compound

Using an ultraviolet-visible spectrophotometer (model U-3120, manufactured and sold by Hitachi, Ltd., Japan), a hydrolysis reaction system was subjected to the measurement of the ultraviolet-visible absorption spectrum between 200 nm and 800 nm. A discolored compound contained in the hydrolysis reaction system was analyzed by determining the wave length at an absorption maximum and the height of the peak.

(8) NMR

Organic impurity compounds were analyzed by measuring each of $^1$H-NMR spectrum and $^{13}$C-NMR spectrum in heavy water. The $^1$H-NMR analysis was conducted using "JNM-α400" (manufactured and sold by JEOL LTD., Japan) and the $^{13}$C-NMR analysis was conducted using "AC-200" (manufactured and sold by Bruker Instruments, Germany). A sample for NMR was prepared by drying the hydrolysis reaction system under reduced pressure to obtain a dried matter, dissolving the obtained dried matter in heavy water, and adding thereto 4,4-dimethyl-4-silane-pentanesulfonic acid sodium salt (δ=0.015 ppm) as an internal standard.

EXAMPLE 1

(1) Synthesis of Glycinonitrile

An 8-liter autoclave equipped with an agitator and a jacket (wherein the autoclave is manufactured and sold by Asahi Kasei Kabushiki Kaisha, Japan) was used as a reactor. The inside of the reactor was purged with nitrogen gas, and 1,200 g of a 37% aqueous formaldehyde solution and hydrogen cyanide in an amount equivalent to the amount of the formaldehyde were added to the reactor, and the formaldehyde and hydrogen cyanide were reacted with each other to thereby obtain an aqueous glycolonitrile solution. To the obtained aqueous glycolonitrile solution was added 5,000 g of a 25% aqueous ammonia solution, and a reaction was performed for 2 hours, thereby obtaining a reaction mixture containing glycinonitrile synthesized. Next, unreacted ammonia and excess water both present in the reaction mixture were removed under reduced pressure by means of a thin film distillation apparatus, to thereby obtain a 30% by weight aqueous glycinonitrile solution. The obtained aqueous glycinonitrile solution was analyzed by liquid chromatography, and the analysis showed that the glycinonitrile solution contained 0.8% by weight of iminodiacetonitrile in addition to glycinonitrile. Further, the aqueous glycinonitrile solution was analyzed by gel permeation chromatography, and the analysis showed that 1.2% by weight of at least one organic impurity compound having a molecular weight of 95 or more was contained in the aqueous glycinonitrile solution.

In addition, the aqueous glycinonitrile solution was analyzed by $^{13}$C-NMR. It was found that in addition to the peaks ascribed to glycinonitrile and iminodiacetonitrile, a peak was present around 60 ppm to 70 ppm in the NMR spectrum. When the absorbance of the aqueous glycinonitrile solution was determined, it was found that absorption maximums were observed at 344 nm and 468 nm, and the absorbances at 344 nm and 468 nm, in terms of a value as measured using a 10 mm quartz cell, were 0.297 and 0.08, respectively.

(2) Culturing of a Microorganism

*Acinetobacter* sp. AK226 (FERM BP-2451) was cultured at 30° C. for 1 day in a medium having the following composition.

Medium (The medium was prepared by dissolving the below-mentioned components in distilled water, and had a pH value of 7.5)

| fumaric acid | 1.0% by weight |
| --- | --- |
| meat extract | 1.0 |
| peptone | 1.0 |
| sodium chloride | 0.1 |
| ε-caprolactam | 0.3 |
| potassium(I) phosphate | 0.2 |
| magnesium sulfate heptahydrate | 0.02 |
| ammonium chloride | 0.1 |
| iron(II) sulfate heptahydrate | 0.003 |
| manganese chloride tetrahydrate | 0.002 |
| cobalt chloride hexahydrate | 0.002 |

(3) Hydrolysis of Glycinonitrile

The cells of the cultured microorganism were collected from the culture broth by centrifugation and washed three times with distilled water. Then, distilled water was added to the washed microorganism so as to obtain a microbial suspension containing the microorganism in an amount of 18.0% by weight in terms of the dry weight of the microorganism. The inside of a 200 ml glass autoclave was purged with nitrogen gas, and 53.3 g of the 30% by weight aqueous glycinonitrile solution synthesized in step (1) above and 46.7 g of distilled water were added thereto under a nitrogen atmosphere. Subsequently, 1.0 g of the microbial suspension was added to the autoclave, and a reaction was initiated at 40° C. At this time, the pH value of the reaction system in the autoclave was approximately 7. After the start of the reaction, the pH value of the reaction system began to increase. Two hours after the start of the reaction, the pH value became 10. The reaction was performed for 10 hours, thereby obtaining a reaction mixture in an amount of 100 g. 2 g of the reaction mixture was taken out. With respect to the taken-out reaction mixture, the amounts of glycinonitrile as a raw material and glycine produced were determined by liquid chromatography, and the amount of ammonia was determined by the Nessler's method. The results of the liquid chromatography showed that glycinonitrile used as a raw material had completely disappeared from the reaction system and the yield of glycine was 99%. Ammonia was stoichiometrically produced. The amount of glycine produced per gram (dry weight) of the microorganism was 117 g/g and the activity for glycine production was 12 g/g·Hr.

The remaining 98 g of the reaction mixture was centrifuged while cooling, to thereby separate the microorganism and recover a supernatant. The recovered supernatant was subjected to filtration under pressure by means of an ultrafiltration membrane to thereby remove the residual cells of the microorganism and proteins from the supernatant and obtain a filtrate. 2 ml of the filtrate was taken out and subjected to the measurement of the ultraviolet-visible absorption spectrum, and it was found that the absorbance at 468 nm was 0.79. The remainder of the filtrate was subjected to distillation by means of a thin film distillation apparatus to thereby separate ammonia and excess water from the filtrate by evaporation. As a result, when the condensate and the ice and liquid recovered in a dry ice-ethanol trap were combined together, 48 g of an aqueous ammonia solution was obtained. 43 g of a concentrated glycine solution was recovered from the bottom of the distillation apparatus. The concentrated glycine solution was cooled to room temperature to thereby separate glycine by crystal-deposition. The crystals obtained by conducting the crystal-deposition operation only once were dried, thereby obtaining 16.5 g of glycine crystals. The purity of the obtained glycine was 99.99%.

COMPARATIVE EXAMPLE 1

The influence of organic impurity compounds which are by-products contained in an aqueous glycinonitrile solution was analyzed in the following manner. A 30% by weight aqueous glycinonitrile solution obtained in the same manner as in Example 1 was heated at 90° C. under a flow of nitrogen gas. The steam generated by heating and entrained by the nitrogen gas was captured by a dry ice-ethanol trap. 10 ml of the heated glycinonitrile solution was sampled at the time points of 15 minutes, 30 minutes and 1 hour after the start of the heating, and, thereafter, the sampling was further performed every 30 minutes until 5 hours passed from the start of the heating. The solution samples (11 samples in total) were stored under cooling.

A part of each of the solution samples was individually analyzed by liquid chromatography, gel permeation chromatography, ultraviolet-visible absorption spectrometry and $^{13}$C-NMR. The glycinonitrile solution which was heated for 30 minutes or longer had an odor of ammonia. Although the glycinonitrile solution was concentrated in accordance with the lapse of the heating time, the heated glycinonitrile solution had a glycinonitrile concentration within the range of from 30 to 35% by weight. From these results, it was found that the glycinonitrile contained in the glycinonitrile solution had been denatured by the heating. Further, the amounts of organic impurity compounds having molecular weights of 95 or more increased with the lapse of the heating time. The organic impurity compounds included iminodiacetonitrile and further included at least one compound which exhibits a peak between 50 ppm and 90 ppm in the $^{13}$C-NMR spectrum and at least one compound which exhibits absorption maximums at 380 nm and 468 nm in the ultraviolet-visible absorption spectrum.

The hydrolytic activity of a microorganism to produce glycine from an aqueous glycinonitrile solution was evaluated with respect to each of the above-obtained 11 samples of heated, aqueous glycinonitrile solution and in one sample of a non-heated, aqueous glycinonitrile solution (that is, 12 samples in total), and a comparison was made among the 12 samples with respect to the exhibited hydrolytic activity. The procedure was as follows. Using a nitrogen box, 5.0 ml of each of the glycinonitrile solution samples was individually charged into a test tube, and 5.0 ml of distilled water was added thereto. Next, using Acinetobacter sp. AK226, a microbial suspension containing the microorganism in an amount of 12.5% by weight in terms of the dry weight of the microorganism was prepared in the same manner as in Example 1. 0.5 ml of the prepared microbial suspension was added to each test tube and the test tubes were hermetically sealed using Parafilm. The hermetically sealed test tubes were set in a thermostatic shaker placed in a nitrogen box, and a hydrolysis reaction was performed at 30° C. for 8 hours, thereby obtaining a reaction mixture in each test tube. 2 g of the reaction mixture was taken out and analyzed by liquid chromatography. The results are shown in Table 1. As shown in Table 1, it was found that the yield of glycine depends on the concentration of the organic impurity compounds, and when the concentration of the organic impurity compounds exceed 10% by weight, the yield of glycine decreases markedly (see the results of Samples 11 and 12). Almost all matter other than glycine in the reaction mixture was unreacted glycinonitrile, and from acted glycinonitrile, and from this fact, it is considered that the organic impurity compounds had markedly inhibited the activity of the microbial enzyme. On the other hand, when the concentration of the organic impurity compounds was 5% by weight or less, the yield of glycine was 90% or more, and when the concentration of the organic impurity compounds was 1% by weight or less, the yield of glycine was the same as that obtained in the case of the non-heated glycinonitrile solution.

TABLE 1

| Sample No. | Heating time (hr) | Concentration of organic impurity compounds (% by weight) | Yield of glycine |
|---|---|---|---|
| 1 | 0.0 | 0.5% | 98% |
| 2 | 0.25 | 1.0% | 98% |
| 3 | 0.5 | 1.5% | 96% |
| 4 | 1.0 | 2.0% | 96% |
| 5 | 1.5 | 3.0% | 90% |
| 6 | 2.0 | 5.0% | 91% |
| 7 | 2.5 | 6.5% | 84% |
| 8 | 3.0 | 7.0% | 80% |
| 9 | 3.5 | 9.0% | 79% |
| 10 | 4.0 | 10.0% | 70% |
| 11 | 4.5 | 13.0% | 13% |
| 12 | 5.0 | 18.0% | 4% |

EXAMPLE 2

(1) Synthesis of Glycinonitrile

A 30% by weight aqueous glycinonitrile solution was synthesized in the same manner as in Example 1.

(2) Culturing of a Microorganism

Acinetobacter sp. AK226 was cultured in the same manner as in Example 1.

(3) Hydrolysis of Glycinonitrile

The cells of the cultured microorganism were collected from the culture broth by centrifugation and washed three times with distilled water. Then, distilled water was added to the washed microorganism so as to obtain a microbial suspension containing the microorganism in an amount of 5.0% by weight in terms of the dry weight of the microorganism. The inside of a pressure resistant Schlenk's tube used as a reactor was purged with nitrogen gas, and 1.0 ml of the microbial suspension and 16 ml of distilled water were added thereto under a flow of nitrogen gas, followed by addition of 3 ml of the aqueous glycinonitrile solution. Then, the pressure resistant Schlenk's tube was hermetically sealed and a reaction was initiated at 20° C. At this time, the pH value of the reaction system in the pressure resistant Schlenk's tube was approximately 7. Two hours after the start of the reaction, the pH value became 10.1. A part of the reaction system was taken out and analyzed by liquid chromatography. The results of the liquid chromatography showed that glycinonitrile used as a raw material had disappeared from the reaction system and glycine was stoichiometrically produced. Based on the above results, an operation which comprises elevating the reaction temperature by 5° C. and simultaneously adding 3 ml of the 30% by weight aqueous glycinonitrile solution (enzyme substrate) to the reactor was repeated every 2 hours during the reaction until the operation was performed 4 times. The reaction was performed for 10 hours in total, thereby obtaining a reaction mixture in an amount of 32 ml. 2 ml of the reaction mixture was taken out and analyzed in the same manner as in Example 1. As a result, it was found that glycinonitrile used as a raw material had completely disappeared from the reaction system and the yield of glycine was 100%. Ammonia was stoichiometrically produced. The amount of glycine produced per gram (dry weight) of the microorganism was 120 g/g and the activity for glycine production was 12 g/g·Hr.

The remaining 30 ml of the reaction mixture was centrifuged while cooling to obtain a supernatant, and the obtained supernatant was subjected to ultrafiltration, thereby obtaining a filtrate. The obtained filtrate was concentrated using a rotary evaporator to thereby obtain a concentrated glycine solution. The concentrated glycine solution was cooled to thereby separate glycine by crystal-deposition. The crystals were recovered by filtration and then dried, thereby obtaining 4.6 g of glycine crystals. The purity of the obtained glycine was 99.99%.

EXAMPLE 3

(1) Synthesis of Glycinonitrile

A 30% by weight aqueous glycinonitrile solution was synthesized in the same manner as in Example 1.

(2) Culturing of a Microorganism

Acinetobacter sp. AK226 was cultured in the same manner as in Example 1.

(3) Hydrolysis of Glycinonitrile

The cells of the cultured microorganism were collected from the culture broth by centrifugation and washed three times with distilled water. Then, distilled water was added to the washed microorganism so as to obtain a microbial suspension containing the microorganism in an amount of 12.5% by weight in terms of the dry weight of the microorganism. The inside of a 200 ml glass autoclave was purged with nitrogen gas, and 53.3 g of the 30% by weight aqueous glycinonitrile solution synthesized in step (1) above and 41.7 g of distilled water were added thereto under a nitrogen atmosphere. Subsequently, 5 g of the microbial suspension was added to the autoclave, and a reaction was initiated at 50° C. At this time, the pH value of the reaction system in the autoclave was approximately 7. After the start of the reaction, the pH value of the reaction system began to increase. One hour after the start of the reaction, the pH value became 10. The reaction was performed for 8 hours, thereby obtaining a reaction mixture in an amount of 100 g. 2 g of the reaction mixture was taken out and analyzed in the same manner as in Example 1. As a result, it was found that glycinonitrile used as a raw material had completely disappeared from the reaction system and the yield of glycine was 99%. Ammonia was stoichiometrically produced. The amount of glycine produced per gram (dry weight) of the microorganism was 168 g/g and the activity for glycine production was 21 g/g·Hr.

The reaction mixture was subjected to centrifugation, ultrafiltration and thin film distillation in the same manner as in Example 1, thereby obtaining 48 g of aqueous ammonia and 43 g of a concentrated glycine solution. Glycine contained in the concentrated glycine solution was crystallized and dried, thereby obtaining 17 g of glycine crystals. The purity of the obtained glycine was 99.99%.

EXAMPLE 4

The cells of the microorganism recovered by centrifugation in Example 3 were washed three times with distilled water. Then, distilled water was added to the washed microorganism so as to obtain 5 g of a microbial suspension. By using the obtained microbial suspension, glycine was produced in substantially the same manner as in Example 3. Specifically, the inside of a 200 ml glass autoclave was purged with nitrogen gas, and 50.0 g of a 30% by weight aqueous glycinonitrile solution synthesized in the same manner as in step (1) of Example 1 and 45.0 g of distilled water were added thereto under a nitrogen atmosphere. Subsequently, 5 g of the microbial suspension was added to the autoclave, and a reaction was initiated at 50° C. The reaction was performed for 8 hours, thereby obtaining a reaction mixture in an amount of 100 g. 2 g of the reaction mixture was taken out and analyzed in the same manner as in Example 1. As a result, it was found that glycinonitrile used as a raw material had completely disappeared from the reaction system and the yield of glycine was 99%. Ammonia was stoichiometrically produced. The amount of glycine produced per gram (dry weight) of the microorganism was 157 g/g and the activity for glycine production was 20 g/gHr. The sum of amounts of glycine products produced per gram (dry weight) of the microorganism in Examples 3 and 4 was 325 g/g and the overall activity for glycine production was 20 g/g·Hr.

The remainder of the reaction mixture was subjected to centrifugation, ultrafiltration and thin film distillation in the same manner as in Example 1, thereby obtaining 48 g of aqueous ammonia and 42 g of a concentrated glycine solution. Glycine contained in the concentrated glycine solution was crystallized and dried, thereby obtaining 16 g of glycine crystals. The purity of the obtained glycine was 99.99%.

EXAMPLE 5

The cells of the microorganism recovered by centrifugation in Example 4 were washed three times with distilled water. Then, distilled water was added to the washed microorganism so as to obtain 5 g of a microbial suspension. By using the obtained microbial suspension, glycine was produced in substantially the same manner as in Example 3. Specifically, the inside of a 200 ml glass autoclave was purged with nitrogen gas. and 43.3 g of a 30% by weight aqueous glycinonitrile solution synthesized in the same manner as in step (1) of Example 1 and 51.7 g of distilled water were added thereto under a nitrogen atmosphere. Subsequently, 5 g of the microbial suspension was added to the autoclave, and a reaction was initiated at 50° C. The reaction was performed for 8 hours, thereby obtaining a reaction mixture in an amount of 100 g. 2 g of the reaction mixture was taken out and analyzed in the same manner as in Example 1. As a result, it was found that glycinonitrile used as a raw material had completely disappeared from the reaction system and the yield of glycine was 99%. Ammonia was stoichiometrically produced. The amount of glycine produced per gram (dry weight) of the microorganism was 136 g/g and the activity for glycine production was 17 g/g·Hr. The sum of amounts of glycine products produced per gram (dry weight) of the microorganism in Examples 3, 4 and 5 was 461 g/g and the overall activity for glycine production was 19 g/g·Hr.

EXAMPLE 6

(1) Synthesis of Glycinonitrile

A 30% by weight aqueous glycinonitrile solution was synthesized in the same manner as in Example 1.

(2) Culturing of a Microorganism

*Rodococcus maris* BP-479-9 (FERM BP-5219) was cultured at 30° C. for 1 day in a medium having the following composition.

Medium (The medium was prepared by dissolving the below-mentioned components in distilled water, and had a pH value of 7.5)

| | |
|---|---|
| glycerin | 1.0% by weight |
| meat extract | 1.0 |
| peptone | 1.0 |
| sodium chloride | 0.1 |
| ε-caprolactam | 0.3 |
| potassium(I) phosphate | 0.2 |
| magnesium sulfate heptahydrate | 0.02 |
| ammonium chloride | 0.1 |
| iron(II) sulfate heptahydrate | 0.003 |
| manganese chloride tetrahydrate | 0.002 |
| cobalt chloride hexahydrate | 0.002 |

(3) Hydrolysis of Glycinonitrile

The cells of the cultured microorganism were collected from the culture broth by centrifugation and washed three times with distilled water. Then, distilled water was added to the washed microorganism so as to obtain a microbial suspension containing the microorganism in an amount of 6.0% by weight in terms of the dry weight of the microorganism. By using 1.0 ml of the obtained microbial suspension, glycine was produced in substantially the same manner as in Example 2. Specifically, the hydrolysis reaction of glycinonitrile was performed for 10 hours, thereby obtaining a reaction mixture in an amount of 32 g. 2 g of the reaction mixture was taken out and analyzed in the same manner as in Example 1. As a result, it was found that glycinonitrile used as a raw material had completely disappeared from the reaction system and the yield of glycine was 100%. Ammonia was stoichiometrically produced. The amount of glycine produced per gram (dry weight) of the microorganism was 100 g/g and the activity for glycine production was 10.0 g/g·Hr.

The remainder of the reaction mixture was treated in the same manner as in Example 1, thereby obtaining 4.6 g of glycine crystals.

EXAMPLE 7
(1) Synthesis of Glycinonitrile

A 30% by weight aqueous glycinonitrile solution was synthesized in the same manner as in Example 1.

(2) Culturing of a Microorganism

*Corynebacterium nitrilophilus* (ATCC 21419) was cultured in the same manner as in Example 6.

(3) Hydrolysis of Glycinonitrile

The cells of the cultured microorganism were collected from the culture broth by centrifugation and washed three times with distilled water. Then, distilled water was added to the washed microorganism so as to obtain a microbial suspension containing the microorganism in an amount of 8.0% by weight in terms of the dry weight of the microorganism. By using 1.0 ml of the obtained microbial suspension, glycine was produced in substantially the same manner as in Example 2. Specifically, the hydrolysis reaction of glycinonitrile was performed for 10 hours, thereby obtaining a reaction mixture in an amount of 32 g. 2 g of the reaction mixture was taken out and analyzed in the same manner as in Example 1. As a result, it was found that glycinonitrile used as a raw material had completely disappeared from the reaction system and the yield of glycine was 99%. Ammonia was stoichiometrically produced. The amount of glycine produced per gram (dry weight) of the microorganism was 75 g/g and the activity for glycine production was 8 g/g·Hr.

The remainder of the reaction mixture was treated in the same manner as in Example 1, thereby obtaining 4.6 g of glycine crystals.

EXAMPLE 8
(1) Synthesis of Glycinonitrile

A 30% by weight aqueous glycinonitrile solution was synthesized in the same manner as in Example 1.

(2) Culturing of a Microorganism

*Corynebacterium* sp. C5 was cultured in the same manner as in Example 6.

(3) Hydrolysis of Glycinonitrile

The cells of the cultured microorganism were collected from the culture broth by centrifugation and washed three times with distilled water. Then, distilled water was added to the washed microorganism so as to obtain a microbial suspension containing the microorganism in an amount of 12.5% by weight in terms of the dry weight of the microorganism. There was provided a reactor comprised of a 1,000 ml separable three-necked flask which was equipped with an agitator, a jacket for maintaining a constant temperature, a nitrogen gas introduction nozzle which extends to the bottom of the separable flask, a mist separator connected to a dry ice trap, a thermometer and a tube for sampling a reaction mixture. 9 ml of the microbial suspension was charged into the separable flask and, then, 30 ml of the 30% by weight aqueous glycinonitrile solution and 161 ml of distilled water were added thereto. A reaction was initiated at 30° C., and the reaction was performed while feeding nitrogen gas into the separable flask at a rate of 3 liters/hour, using a gas flow meter. 1 hour after the start of the reaction, 30 ml of the 30% by weight aqueous glycinonitrile solution was further added to the separable flask. The addition of the aqueous glycinonitrile solution was performed every 1 hour 3 more times, and the reaction was conducted for 5 hours in total, thereby obtaining a reaction mixture and by-products. The by-products were recovered in the dry ice trap, and when the ice and liquid recovered in the dry ice trap were combined together, 15 g of the by-products was obtained. The obtained by-products were dissolved in 50 ml of water, and with respect to the resultant solution, the amount of ammonia was determined by the Nessler's method. It was found that 14 g of ammonia had been recovered in the dry ice trap. The reaction mixture was obtained in an amount of 305 g. 2 g of the reaction mixture was taken out and analyzed in the same manner as in Example 1. As a result, it was found that glycinonitrile used as a raw material had disappeared from the reaction system and the yield of glycine was 99%. Further, a trace amount of ammonia had remained in the reaction mixture. The amount of glycine produced per gram (dry weight) of the microorganism was 53 g/g and the activity for glycine production was 11 g/g·Hr.

The remaining 303 g of the reaction mixture was treated in the same manner as in Example 1, thereby obtaining 47 g of glycine crystals.

EXAMPLE 9
(1) Synthesis of Glycinonitrile

A 30% by weight aqueous glycinonitrile solution was synthesized in the same manner as in Example 1.

(2) Culturing of a Microorganism

*Alcaligenes faecalis* IFO 13111 (FERM BP-4750) was cultured in the same manner as in Example 6.

(3) Hydrolysis of Glycinonitrile

The cells of the cultured microorganism were collected from the culture broth by centrifugation and washed three times with distilled water. Then, distilled water was added to the washed microorganism so as to obtain a microbial suspension containing the microorganism in an amount of 12.5% by weight in terms of the dry weight of the microorganism. There was provided a reactor comprised of a 1,000 ml separable three-necked flask which was equipped with an agitator, a jacket for maintaining a constant temperature, a nitrogen gas introduction nozzle which extends to the bottom of the separable flask, a single column distillation tower which is connected to a vacuum pump through a dry ice trap, a pressure sensor, a thermometer and a tube for sampling a reaction mixture wherein the tube is connected to a liquid transfer pump. 11 ml of the microbial suspension was charged into the separable flask and, then, 30 ml of the 30% by weight aqueous glycinonitrile solution and 159 ml of distilled water were added thereto. A reaction was initiated at 30° C., and the reaction was performed while feeding nitrogen gas into the separable flask at a rate of 3 liters/hour, using a gas flow meter. 1 hour after the start of the reaction, 30 ml of the 30% by weight aqueous glycinonitrile solution was further added to the separable flask. The addition of the aqueous glycinonitrile solution was performed every 1 hour 3 more times, and the reaction was conducted for 5 hours in total, thereby obtaining a reaction mixture and by-products. The by-products were recovered in the dry ice trap, and when the ice and liquid recovered in the dry ice trap were combined together, 25 g of the by-products were obtained. The obtained by-products were dissolved in 50 ml of water, and with respect to the resultant solution, the amount of ammonia was determined by the Nessler's method. It was found that 15 g of ammonia had been recovered in the dry ice trap. The reaction mixture was obtained in an amount of 295 g. 2 g of the reaction mixture was taken out and analyzed in the same manner as in Example 1. As a result, it was found that glycinonitrile used as a raw material had disappeared from the reaction system and the yield of glycine was 99%. Further, a trace amount of ammonia had remained in the reaction mixture. The amount of glycine produced per gram (dry weight) of the microorganism was 42 g/g and the activity for glycine production was 9 g/g·Hr.

The remaining 293 g of the reaction mixture was treated in the same manner as in Example 1, thereby obtaining 48 g of glycine crystals.

EXAMPLE 10

(1) Synthesis of Glycinonitrile

A 30% by weight aqueous glycinonitrile solution was synthesized in the same manner as in Example 1.

(2) Culturing of a Microorganism

The below-mentioned microorganisms were individually cultured in the same manner as in Example 6.

Microorganisms

Acinetobacter sp. AK227 (FERM BR-7413)
Mycobacterium sp. AC777 (PERM BR-2352)
Rhodopseudomonas spheroides (ATCC 11167)
Candida tropicalis (ATCC 20311)
Pseudomonas sp. 88-SB-CN5
Acremonium sp. D9K
Klebsiella sp. D5B (3) Hydrolysis of Glycinonitrile With resect to each of the cultured microorganisms, the following procedure was individually performed. The cells of the cultured microorganism were collected from the culture broth by centrifugation and washed three times with distilled water. Then, distilled water was added to the washed microorganism so as to obtain a microbial suspension containing the microorganism in an amount of 12.5% by weight in terms of the dry weight of the microorganism. By using the obtained microbial suspension, glycine was produced in the following manner. The inside of a 200 ml glass autoclave was purged with nitrogen gas, and 53.3 g of the 30% by weight aqueous glycinonitrile solution synthesized in step (1) above and 42.7 g of distilled water were added thereto under a nitrogen atmosphere. Subsequently, 4.0 g of the microbial suspension was added to the autoclave, and a reaction was initiated at 40° C. The reaction was performed for 8 hours, thereby obtaining a reaction mixture in an amount of 100 g. 2 g of the reaction mixture was taken out. With respect to the taken-out reaction mixture, the amounts of glycinonitrile as a raw material and glycine produced were determined by liquid chromatography, and the amount of ammonia was determined by the Nessler's method. The results are shown in Table 2. As shown in Table 2, in the case of any of the employed microorganisms, glycinonitrile used as a raw material had completely disappeared from the reaction system, and glycine was produced in high yield. Further, ammonia was stoichiometrically produced.

TABLE 2

| Microbial strain used | Conversion of glycinonitrile (%) | Yield of glycine (%) |
| --- | --- | --- |
| Acinetobacter sp. AK227 | 100 | 100 |
| Mycobacterium sp. AC777 | 100 | 99 |
| Rhodopseudomonas spheroides | 100 | 97 |
| Candida tropicalis | 100 | 97 |
| Pseudomonas sp. 88-SB-CN5 | 100 | 100 |
| Acremonium sp. D9K | 100 | 97 |
| Klebsiella sp. D5B | 100 | 97 |

EXAMPLE 11

(1) Synthesis of Glycinonitrile

A 30% by weight aqueous glycinonitrile solution was synthesized in the same manner as in Example 1.

The absorbance of the aqueous glycinonitrile solution at 468 nm was determined. It was found that the absorbance, in terms of a value as measured using a 10 mm quartz cell and at a concentration of 1 mol of glycinonitrile per liter, was 0.08.

(2) Culturing of a Microorganism

The below-mentioned microorganisms were individually cultured in the same manner as in Example 6.

Microorganisms

Acinetobacter sp. AK226 (FERM BP-2451)
Rhodococcus maris BP-479-9 (FERM BP-5219)
Corynebacterium sp. C5 (FERM BP-7414)
Corynebacterium nitrilophilus (ATCC 21419)
Alcaligenes faecalis IFO 13111 (FERM BP-4750).

(3) Hydrolysis of Glycinonitrile

With resect to each of the cultured microorganisms, the following procedure was individually performed. The cells of the cultured microorganisms were collected from the culture broth by centrifugation and washed three times with distilled water. Then, distilled water was added to the washed microorganism so as to obtain a microbial suspension containing the microorganism in an amount of 12.5% by weight in terms of the dry weight of the microorganism. By using the obtained microbial suspension and a reductive compound shown in Table 3, glycine was produced in the following manner. The inside of a 200 ml glass autoclave was purged with nitrogen gas, and 53.3 g of the 30% by weight aqueous glycinonitrile solution synthesized in step (1) above and 42.7 g of distilled water were added thereto under a nitrogen atmosphere, followed by addition of a reductive compound shown in Table 3. Then, the microbial suspension was added to the autoclave in an amount (weight) shown in Table 3. When the amount of the microbial suspension used was less than 5 g, distilled water was also added to the autoclave in an amount such that the total weight of the microbial suspension and the distilled water became 5 g. A reaction was initiated at 30° C. and performed for 10 hours. With respect to each of the microorganisms used, for comparison, an experiment was also performed which did not use a reductive compound. Further, with respect to Acinetobacter sp. AK226, in order to make a comparison between the effects obtained by using an open reaction system and the effects obtained by using a closed reaction system, an experiment was also conducted using an open reaction system and not using a reductive compound. 100 g of a reaction mixture was obtained in each experiment and 2 g of the reaction mixture was taken out. With respect to the taken-out reaction mixture, the amount of ammonia was determined by the Nessler's method, and the amounts of glycinonitrile as a raw material and glycine produced were determined by liquid chromatography.

The remainder of the reaction mixture was subjected to refrigerating centrifugation and ultrafiltration in the same manner as in Example 1 to thereby obtain a glycine solution. A portion of the obtained glycine solution was taken out and subjected to the measurement of the absorbance at 468 nm. Glycine crystals were recovered from the remaining glycine solution by conducting thin film distillation, crystal-deposition (once), and drying. The purity of the recovered glycine was determined. The results are shown in Table 3.

Discoloration of glycine was greatly suppressed by the addition of a reductive compound. Further, the yield of glycine was greatly improved and the purity of glycine crystals was 99.99%. On the other hand, when the reaction was conducted in an open reaction system, a brown discolored reaction mixture was obtained and the yield of glycine was lowered. In the case of the brown discolored reaction mixture, ultrafiltration of the reaction mixture was difficult, and the obtained glycine crystals were discolored and the purity thereof was lowered to 99%.

7 at a feeding rate of 82 normal liters/hr through a mass flow controller. The reaction temperature of autoclave 7 was set at 5° C. and the reaction for producing glycinonitrile was initiated. Generation of heat due to the absorption of ammonia was observed at the start of the reaction, but thereafter the reaction proceeded at the set reaction temperature and pressure. The residence time in autoclave 7 was adjusted to

TABLE 3

| Microorganism | Microbial suspension (g) | Reductive compound | Amount added (mg) | Absorption before reaction | Absorption after reaction* | Yield of glycine (%) | Purity of glycine (%) |
|---|---|---|---|---|---|---|---|
| Acinetobacter sp. AK226 | 2.4 | Reaction in an open reaction system | 0 | 0.08 | 3.40 | 90 | 99.00 |
| | | None | 0 | 0.08 | 0.79 | 97 | 99.99 |
| | | L-ascorbic acid | 101 | 0.08 | 0.10 | 100 | 99.99 |
| | | Diammonium sulfite monohydrate | 43 | 0.08 | 0.10 | 100 | 99.99 |
| Rhodococcus maris BP-479-9 | 3.0 | None | 0 | 0.08 | 0.79 | 97 | 99.99 |
| | | Formic acid | 53 | 0.08 | 0.12 | 100 | 99.99 |
| | | Sodium sulfite | 36 | 0.08 | 0.19 | 99 | 99.99 |
| Corynebacterium nitrilophilus | 4.0 | None | 0 | 0.08 | 0.79 | 100 | 99.99 |
| | | L-cysteine | 70 | 0.08 | 0.11 | 100 | 99.99 |
| | | Methylformate | 69 | 0.08 | 0.33 | 100 | 99.99 |
| Corynebacterium sp. C5 | 5.0 | None | 0 | 0.08 | 0.79 | 96 | 99.99 |
| | | Flutatione | 175 | 0.08 | 0.11 | 100 | 99.99 |
| | | Ammonium formate | 72 | 0.08 | 0.14 | 100 | 99.99 |
| | | Potassium sulfite | 37 | 0.08 | 0.33 | 99 | 99.99 |
| Alcaligenes faecalis | 6.25 | None | 0 | 0.08 | 0.79 | 95 | 99.99 |
| | | L-cysteine hydrochloride monohydrate | 100 | 0.08 | 0.11 | 100 | 99.99 |
| | | Ethyl formate | 85 | 0.08 | 0.19 | 100 | 99.99 |

*Absorption at 468 nm (in terms of a value as measured using a 10 mm quartz cell and at a concentration of 1 mol of glycine per liter).

EXAMPLE 12

Continuous production of glycine is explained below in detail with reference to the production system shown in FIG. 1.

(1) Synthesis of Glycinonitrile

1-Liter stainless steel autoclaves 6, 7 and 8 which are individually equipped with an agitator, a level sensor, a pressure gauge, a safety valve and a temperature indicator, and flash distillation apparatus 9 were connected with each other in series. Glycinonitrile was synthesized in the following manner. Before conducting the reaction, the inside of autoclaves 6, 7 and 8 and the conduits connecting the autoclaves with each other was purged with nitrogen gas. Three diaphragm pumps were provided and the diaphragm pumps were respectively used for continuously feeding 37% by weight aqueous formaldehyde solution 1 (containing methyl alcohol in an amount of less than 10% by weight) at a feeding rate of 100 g/hr (the aqueous formaldehyde solution 1 had previously been treated for replacing oxygen dissolved therein by nitrogen), liquid hydrogen cyanide 2 at a feeding rate of 33.3 g/hr, and distilled water containing 100 ppm of 4% sodium hydroxide 3 at a feeding rate of 240 g/hr into autoclave 6. The reaction temperature was set at 40° C. and the reaction for producing glycolonitrile was initiated. Generation of heat was observed immediately after the start of the reaction, but thereafter the reaction proceeded at the set reaction temperature. Residence time was adjusted to 1 hour by using the level controller, and a reaction mixture containing glycolonitrile was fed from autoclave 6 into autoclave 7 by using a pump, while continuously feeding ammonia gas 4 under a pressure of 0.2 MPa into autoclave 7 at a feeding rate of 82 normal liters/hr through a mass flow controller. The reaction temperature of autoclave 7 was set at 5° C. and the reaction for producing glycinonitrile was initiated. Generation of heat due to the absorption of ammonia was observed at the start of the reaction, but thereafter the reaction proceeded at the set reaction temperature and pressure. The residence time in autoclave 7 was adjusted to 1 hour by using a level controller. and a reaction mixture was fed from autoclave 7 into autoclave 8 by using a pump. The temperature of autoclave 8 was set at 55° C. After the residence time of 1 hour passed, a reaction mixture containing glycinonitrile was continuously withdrawn from autoclave 8 by using a pump. A primary reaction mixture obtained during the first 6 hours from the start of the reaction was collected as a waste and the reaction mixture obtain after 6 hours from the start of the reaction and obtained later was fed into flash distillation apparatus 9 set at the atmospheric pressure. The column top temperature of flash distillation apparatus 9 was set at −20° C., and the reaction mixture was cooled at the column top of distillation apparatus 9. Moisture contained in the reaction mixture was removed by cooling the reaction mixture with ice, and moist ammonia gas was recovered by a dry ice-ethanol trap, thereby obtaining liquid ammonia 10. Recovered liquid ammonia 10 was used as a raw material to be fed into autoclave 7. An aqueous glycinonitrile solution containing a small amount of ammonia was recovered from the column bottom of the flash distillation apparatus, and the recovered glycinonitrile solution was stored at 5° C. in intermediate tank 11. For the storage, 100 ppm of 10% by weight sulfuric acid as a stabilizer was added to the glycinonitrile solution in intermediate tank 11. A 33% by weight glycinonitrile solution was obtained. The obtained glycinonitrile solution contained 0.9% by weight of iminodiacetonitrile and 1.3% by weight of an organic impurity compound having a molecular weight of 95 or more.

(2) Culturing of a Microorganism

*Acinetobacter* sp. AK226 (FERM BP-2451) was cultured in the same manner as in Example 1. The cells of the cultured microorganism were collected from the culture broth by centrifugation and washed three times with distilled water. Then, distilled water was added to the washed microorganism so as to obtain a microbial suspension 5 containing the microorganism in an amount of 12.5% by weight in terms of the dry weight of the microorganism.

(3) Hydrolysis Reaction and Separation of a Microorganism

A 10-liter autoclave equipped with an agitator, a thermometer and a pH sensor was used as hydrolysis reactor 12. 5,400 g of the aqueous glycinonitrile solution stored in intermediate tank 11 was charged into hydrolysis reactor 12 under a flow of nitrogen gas and then, 60 g of microbial suspension 5 prepared in step (2) above was added thereto. The hydrolysis reaction of glycinonitrile was initiated at a set reaction temperature of 50° C. After conducting the reaction for 8 hours, the resultant reaction mixture was transferred into continuous centrifuge 13 (model TA1-02, manufactured and sold by Westfalia Separator Inc., U.S.A.), wherein the microorganism was separated from the reaction mixture by centrifugal filtration. One fifth of the separated microorganism (microorganism slurry) was discarded (microorganism to be discarded 14) and the remainder of the microorganism was washed three times with distilled water. Then, distilled water was added to the washed microorganism so as to obtain 48 g of a recovered microbial suspension. 12 g of a microbial suspension prepared in the same manner as in step (2) above was mixed with the recovered microbial suspension, thereby obtaining 60 g of a microbial suspension. The obtained 60 g of microbial suspension was charged into hydrolysis reactor 12, and a hydrolysis of glycinonitrile was conducted therein in the same manner as mentioned above. In this way, the reaction operation was repeated including the above-described operation for separating and recycling the microorganism. The filtrate obtained by the centrifugal filtration (i.e., the reaction mixture containing glycine) was transferred to circulation type ultrafiltration apparatus 15 (using ultrafiltration membrane: "SIP-1013", manufactured and sold by Asahi Kasei Kabushiki Kaisha, Japan) and concentrated therein while being circulated. The resultant concentrated reaction mixture was transferred to intermediate tank 16 and stored therein. When the volume of the circulating liquid decreased to 500 ml, 500 ml of distilled water was added thereto so that the total volume of the mixture became 1,000 ml, and the mixture was concentrated again until the volume of the circulating liquid became 500 ml. This cycle comprising diluting the liquid and then concentrating the diluted liquid in the ultrafiltration apparatus was performed twice, and then 500 ml of the circulating liquid remaining in ultrafiltration apparatus 15 was discarded.

Step (3) above for producing glycine was repeated to obtain the results shown below, wherein one cycle of step (3) took 12 hours.

The concentrated reaction mixture contained 83% by weight of ammonium salt of glycine and 0.9% by weight of at least one organic impurity compound having a molecular weight of 95 or more.

(4) Recovery of Glycine Crystals

After 18 hours from the start of the reaction in step (1) above, approximately 6 kg of the concentrated reaction mixture was obtained in intermediate tank 16. Then, continuous crystal-deposition of glycine was initiated using the concentrated reaction mixture in intermediate tank 16. The procedure is as described below. The concentrated reaction mixture was flowed through activated carbon column 17, thereby obtaining a concentrate which had been treated with an activated carbon. The obtained activated carbon-treated concentrate was fed into continuous crystal-deposition apparatus 18 at a flow rate of 425 g/hr for performing a crystal-deposition operation. Continuous crystal-deposition apparatus 18 was equipped with an agitator, a level sensor, a thermometer and a vacuum distillation column. Excess water and liquid ammonia contained in the concentrate were removed therefrom by vacuum evaporation at rates of approximately 200 g/hr and approximately 20 g/hr, respectively. The evaporated water and liquid ammonia were, respectively, recovered as distilled water 19 and liquid ammonia 10, and both distilled water 19 and liquid ammonia 10 were recycled for use in the above-mentioned step (1). A slurry (glycine concentration: 40% by weight) was accumulated in a crystal-deposition vessel. A part of the slurry accumulated in the crystal-deposition vessel was intermittently withdrawn from the bottom of the crystal-deposition vessel by suction so that the surface of the slurry in the crystal-deposition vessel was maintained between the predetermined upper and lower levels in the vessel. The withdrawn slurry was subjected to filtration while heating to obtain a filtrate. The obtained filtrate was blown down (blow 20) until the weight thereof exhibited a 4% decrease, to thereby obtain filtrate 21, and filtrate 21 was recycled to the crystal-deposition vessel. The crystal-deposition operation reached a stationary state after 3 hours from the start of the crystal-deposition operation and glycine crystals were deposited in the crystal-deposition vessel. The deposited glycine crystals were taken out from crystal-deposition apparatus 18 and dried to thereby obtain glycine crystals 22. The purity of glycine crystals 22 was determined to be 99.99%. In this production system, glycine was produced at an average rate of 82 g/hr (54 g/g of the microorganism), and the overall yield of glycine was 90% (wherein the overall yield (%) is a value calculated by subtracting all losses (%) in all steps).

INDUSTRIAL APPLICABILITY

By the use of the method of the present invention, a high purity glycine which is useful as a food additive and as a raw material for synthesizing pharmaceuticals, agricultural chemicals and detergents can be produced while achieving advantages in that both the glycine production activity per unit weight of a microorganism and the glycine production activity per unit time become high, and both glycine and ammonia can be stoichiometrically produced without decomposition or consumption thereof and can be separately and easily recovered. Further, glycine can be produced on a commercial scale without causing a heavy burden on the environment.

What is claimed is:

1. A method for producing glycine, comprising:

providing glycinonitrile in the form of an aqueous solution thereof, subjecting the aqueous solution of glycinonitrile to a hydrolysis reaction in a hydrolysis reaction system under the action of a microbial enzyme having the activity to hydrolyze a nitrile group, thereby converting said glycinonitrile to glycine while by-producing ammonia, said hydrolysis reaction system having oxygen dissolved therein in an amount of 5 ppm by weight or less, based on the weight of said hydrolysis reaction system, and containing at least one organic impurity compound inhibiting said microbial enzyme, wherein said at least one organic impurity compound inhibiting said microbial enzyme has a molecular weight of 95 or more and contains at least one member selected from the group consisting of a nitrile group, a carboxyl group, an amide group, an amino group, a hydroxyl group and a trimethyleneamine structure, wherein said trimethyleneamine structure has a skeleton represented by the following formula (1):

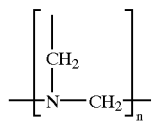 (1)

wherein n represents an integer of 1 or more, said hydrolysis reaction being performed under conditions wherein, during said hydrolysis reaction, the content of said organic impurity compound inhibiting said microbial enzyme in said hydrolysis reaction system is maintained at a level of 10% by weight or less, based on the weight of said hydrolysis reaction system, and isolating the glycine from the hydrolysis reaction system.

2. The method according to claim 1, wherein said at lease one organic impurity compound inhibiting said microbial enzyme is produced as a by-product in at least one reaction selected from the group consisting of the synthesis of glycinonitrile from hydrogen cyanide, formaldehyde and ammonia, and the hydrolysis of the glycinonitrile into glycine and ammonia.

3. The method according to claim 1 or 2, wherein said at least one organic impurity compound inhibiting said microbial enzyme comprises a compound represented by the following formula (2):

$$NH_{3-n}(CH_2Y^1)_n \quad (2)$$

wherein each $Y^1$ independently represents a nitrile group, a carboxyl group or an amide group; and n represents an integer of 2 or 3.

4. The method according to claim 1 or 2, wherein said at least one organic impurity compound inhibiting said microbial enzyme comprises at least one compound selected from the group consisting of the following compounds (a) and (b):

(a) a compound represented by the following formula (3):

 (3)

wherein:
$Y^1$ represents a nitrile group, a carboxyl group or an amide group;
each $Y^2$ independenUy represents an amino group or a hydroxyl group;
n represents an integer of 0 or more; and
the or each $Z^1$ is independently represented by the following formula (4) or (5):

 (4)

 (5)

wherein each $Y^2$ independently represents an amino group or a hydroxyl group, and (b) a compound represented by the following formula (6) or (7):

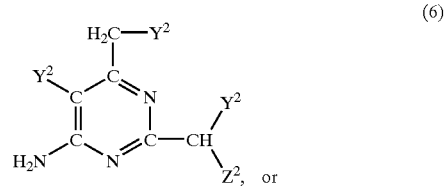 (6)

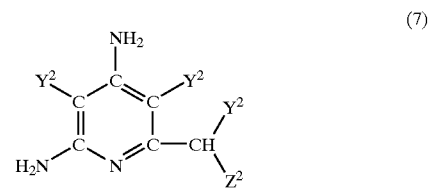 (7)

wherein each $Y^2$ independently represents an amino group or a hydroxyl group; and each $Z^2$ is independently represented by the following formula (8) or (9):

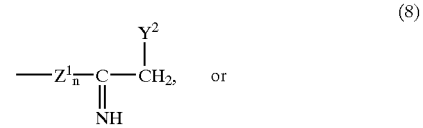 (8)

 (9)

wherein:
$Y^2$ represents an amino group or a hydroxyl group;
the or each $Z^1$ is as defined for formula (3); and
n represents an integer of 0 or more.

5. The method according to claim 1 or 2, wherein said at least one organic impurity compound inhibiting said microbial enzyme comprises at least one compound selected from the group consisting of the following compounds (c) and (d):

(c) a compound represented by the following formula (10) or (11):

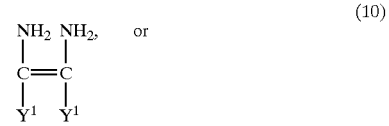 (10)

-continued

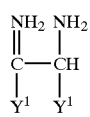
(11)

wherein each $Y^1$ independently represents a nitrile group, a carboxyl group or an amide group, and (d) a compound represented by the following formula (12):

$$(HCN)_n \quad (12)$$

wherein n represents an integer of 4 or more.

6. The method according to claim 1 or 2, wherein said at least one organic impurity compound inhibiting said microbial enzyme comprises a compound having in a molecule thereof at least one skeleton selected from the group consisting of the following skeletons (e) and (f):

(e) a skeleton represented by the following formula (13):

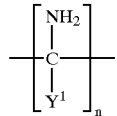
(13)

wherein each $Y^1$ independently represents a nitrile group, a carboxyl group or an amide group; and n represents an integer of 2 or more, and (f) a skeleton represented by the following formula (14) or (15):

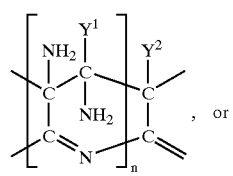
(14)

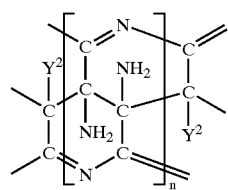
(15)

wherein:
the or each $Y^1$ independently represents a nitrile group, a carboxyl group or an amide group;
each $Y^2$ independently represents an amino group or a hydroxyl group; and
n represents an integer of 1 or more.

7. The method according to claim 1 or 2, wherein said at least one organic impurity compound inhibiting said microbial enzyme comprises a compound having in a molecule thereof at least one skeleton selected from the group consisting of the following skeletons (g) and (h):

(g) a skeleton represented by the following formula (16):

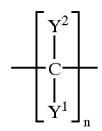
(16)

wherein:
each $Y^1$ independently represents a nitrile group, a carboxyl group or an amide group;
each $Y^2$ independently represents an amino group or a hydroxyl group;
and n represents an integer of 2 or more, and (h) a skeleton represented by the following formula (17) or (18):

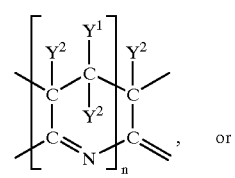
(17)

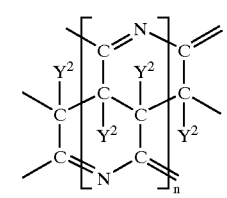
(18)

wherein:
the or each $Y^1$ independently represents a nitrile group, a carboxyl group or an amide group;
each $Y^2$ independently represents an amino group or a hydroxyl group; and
n represents an integer of 1 or more.

8. The method according to claim 1 or 2, wherein said at least one organic impurity compound inhibiting said microbial enzyme comprises hexamethylenetetramine.

9. The method according to claim 1, wherein said at least one organic impurity compound inhibiting said microbial enzyme exhibits a peak between 53 ppm and 100 ppm in a $^{13}$C-NMR spectrum as measured in heavy water.

10. The method according to claim 1, wherein said at least one organic impurity compound inhibiting said microbial enzyme exhibits absorption maximums between 340 nm and 380 nm and between 440 nm and 480 nm in an ultraviolet-visible absorption spectrum as measured with respect to said hydrolysis reaction system.

11. The method according to claim 1, wherein said at least one organic impurity compound inhibiting said microbial enzyme has a molecular weight of 130 or more.

12. The method according to claim 1, wherein the amount of said at least one organic impurity compound inhibiting said microbial enzyme is 1% by weight or less, based on the weight of said hydrolysis reaction system.

13. The method according to claim 1, wherein said hydrolysis is conducted using a closed reaction system, a reaction system which is pressurized with an inert gas, a reaction system through which an inert gas is flowed or a reaction system which is under a pressure of less than atmospheric pressure, so that the amount of oxygen dissolved in said hydrolysis reaction system is suppressed.

14. The method according to claim 1, wherein said hydrolysis is conducted in said hydrolysis reaction system having ammonia dissolved therein.

15. The method according to claim 1, wherein said hydrolysis is conducted in said hydrolysis reaction system containing an electrolyte in an amount of 2% by weight or less, based on the weight of the glycinonitrile.

16. The method according to claim 1, wherein said microbial enzyme having the activity to hydrolyze a nitrile group is derived from a microorganism belonging to a genus selected from the group consisting of *Acinetobacter, Rhodococcus, Corynebacterium, Alcaligenes, Mycobacterium, Rhodopseudomonas* and *Candida*.

17. The method according to claim 16, wherein the microbial strain of said *Acinetobacter* is *Acinetobacter* sp. AK226, deposited with the National Institute of Bioscience and Human-Technology, Japan under the accession number FERN BP-2451, or *Acinetobacter* sp. AK227, deposited with the National Institute of Bioscience and Human-Technology, Japan under the accession number FERM BP-7413.

18. The method according to claim 16, wherein the microbial strain of said *Rhodococcus* is *Rhodococcus maris* BP-479-9, deposited with the National Institute of Bioscience and Human-Technology, Japan under the accession number FERM BP-5219.

19. A The method according to claim 16, wherein the microbial strain of said *Corynebacterium* is *Corynebactenium* sp. C5, deposited with the National Institute of Bioscience and Human-Technology, Japan under the accession number FERM BP-7414, or *Corynebacterium nitrilophilus*, deposited with the American Type Culture Collection, U.S.A. under the accession number ATCC 21419.

20. The method according to claim 16, wherein the microbial strain of said *Alcaligenes* is *Alcaligenes faecalis* IFO 13111, deposited with the National Institute of Bioscience and Human-Technology, Japan under the accession number FERM BP-4750.

21. The method according to claim 16, wherein the microbial strain of said *Mycobacterium* is *Mycobacterium* sp. AC777, deposited with the National Institute of Bioscience and Human-Technology, Japan under the accession number FERM BP-2352.

22. The method according to claim 16, wherein the microbial strain of said *Rhodopseudomonas* is *Rhodopseudomonas spheroides*, deposited with the American Type Culture Collection, U.S.A. under the accession number ATCC 11167.

23. The method according to claim 16, wherein the microbial strain of said *Candida* is *Candida tropicalls*, deposited with the American Type Culture Collection, U.S.A. under the accession number ATCC 20311.

24. The method according to claim 1, wherein the isolation of the glycine from said hydrolysis reaction system is conducted while recovering the by-produced ammonia separately from the recovery of glycine.

25. The method according to claim 24, wherein the glycine and the ammonia are separately recovered by at least one operation selected from the group consisting of distillation, reactive distillation, entrainment by an inert gas, ion exchange, extraction, reprecipitation using a poor solvent, and crystal-deposition by concentration or cooling.

26. The method according to claim 25, wherein the ammonia is recovered by distillation, reactive distillation or entrainment by an inert gas, and the glycine is recovered by subjecting a liquid remaining after the recovery of the ammonia to crystal-deposition by concentration or cooling.

27. The method according to claim 1, which comprises:

(1) reacting hydrogen cyanide with formaldehyde in an aqueous medium in the presence of an alkali catalyst in a closed reaction system to obtain glycolonitrile in the form of an aqueous solution thereof, (2) adding ammonia to the aqueous solution of glycolonitrile to effect a reaction between the glycolonitrile and the ammonia, to thereby obtain glycinonitrile in the form of an aqueous solution thereof while producing water, (3) separating most of the ammonia and a part of the water from the obtained aqueous solution of glycinonitrile by distillation to thereby obtain a hydrolysis reaction system containing the glycinonitrile in the form of an aqueous solution thereof and the ammonia remaining unseparated, wherein the separated ammonia is recovered for recycle thereof to step (2), (4) subjecting said hydrolysis reaction system to a hydrolysis reaction under the action of a microbial enzyme produced by a microorganism added in said hydrolysis reaction system which is in a closed system, thereby converting said glycinonitrile to glycine while by-producing ammonia, (5) separating said microorganism and said microbial enzyme by at least one operation selected from the group consisting of centrifugal filtration and membrane filtration, wherein said microorganism and said microbial enzyme are recovered for recycle thereof to step (4), (6) separating a part of organic impurity compounds inhibiting said microbial enzyme which compounds are by-produced in steps (1) to (5) by at least one operation selected from the group consisting of membrane filtration and adsorbent-separation, (7) separating by distillation the ammonia by-produced in step (4) and an excess amount of water which remains in said hydrolysis reaction system after step (4), wherein the separated ammonia is recovered for recycle thereof to step (2), (8) after or simultaneously with step (7), separating said glycine by crystal-deposition, and (9) drying the crystals of said glycine.

28. A method for producing glycine, comprising:

providing glycinonitrile in the form of an aqueous solution thereof, subjecting the aqueous solution of glycinonitrile to a hydrolysis reaction in a hydrolysis reaction system, thereby converting said glycinonitrile to glycine while by-producing ammonia, said hydrolysis reaction system containing at least one organic impurity compound inhibiting a microbial enzyme, wherein said at least one organic impurity compound inhibiting a microbial enzyme has a molecular weight of 95 or more and contains at least one member selected from the group consisting of a nitrile group, a carboxyl group, an amide group, an amino group, a hydroxyl group and a trimethyleneamine structure, wherein said trimethyleneamine structure has a skeleton represented by the following formula (1):

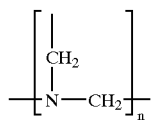

(1)

wherein n represents an integer of 1 or more, said hydrolysis reaction being performed in the presence of ammonia and under conditions wherein, during said hydrolysis reaction, the content of said organic impurity compound inhibiting a microbial enzyme in said hydrolysis reaction system is maintained at a level of 10% by weight or less, based on the weight of said hydrolysis reaction system, and isolating the glycine from the hydrolysis reaction system.

29. The method according to claim 28, wherein the amount of the ammonia is from 0.001 to 5 mol, relative to 1 mole of the glycinonitrile.

30. A method for producing glycine, comprising:

providing glycinonitrile in the form of an aqueous solution thereof, subjecting the aqueous solution of glycinonitrile to a hydrolysis reaction in a hydrolysis reaction system, thereby converting said glycinonitrile to glycine while by-producing ammonia, said hydrolysis reaction system containing at least one organic impurity compound inhibiting a microbial enzyme, wherein said at least one organic impurity compound inhibiting a microbial enzyme has a molecular weight of 95 or more and contains at least one member selected from the group consisting of a nitrile group, a carboxyl group, an amide group, an amino group, a hydroxyl group and a trimethyleneamine structure, wherein said trimethyleneamine structure has a skeleton represented by the following formula (1):

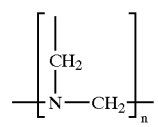

(1)

wherein n represents an integer of 1 or more, said hydrolysis reaction being performed under conditions wherein, during said hydrolysis reaction, the content of said organic impurity compound inhibiting a microbial enzyme in said hydrolysis reaction system is maintained at a level of 10% by weight or less, based on the weight of said hydrolysis reaction system, and isolating the glycine from the hydrolysis reaction system, wherein the isolation of the glycine from said hydrolysis reaction system is conducted while recovering the by-produced ammonia separately from the recovery of glycine in the absence of a base and an acid.

31. The method according to claim 30, wherein the glycine and ammonia are separately recovered by at least one operation selected from the group consisting of distillation, reactive distillation, entrainment by an inert gas, ion exchange, extraction, reprecipitation using a poor solvent, and crystal-deposition by concentration or cooling.

32. The method according to claim 31, wherein the ammonia is recovered by distillation, reactive distillation or entrainment by an inert gas, and the glycine is recovered by subjecting a liquid remaining after the recovery of the ammonia to crystal-deposition by concentration or cooling.

* * * * *